(12) United States Patent
Kasahara et al.

(10) Patent No.: US 8,173,684 B2
(45) Date of Patent: May 8, 2012

(54) PYRIDONE DERIVATIVES AS P38α MAPK INHIBITORS

(75) Inventors: Chiyoshi Kasahara, Chuo-ku (JP); Hitoshi Yamazaki, Chuo-ku (JP)

(73) Assignees: Astellas Pharma Inc., Tokyo (JP); Wakunaga Pharmaceutical Co., Ltd., Osaka-shi (JP)

( * ) Notice: Subject to any disclaimer, the term of this patent is extended or adjusted under 35 U.S.C. 154(b) by 395 days.

(21) Appl. No.: 12/597,926

(22) PCT Filed: May 2, 2008

(86) PCT No.: PCT/JP2008/058689
§ 371 (c)(1),
(2), (4) Date: Oct. 28, 2009

(87) PCT Pub. No.: WO2008/140066
PCT Pub. Date: Nov. 20, 2008

(65) Prior Publication Data
US 2010/0063098 A1    Mar. 11, 2010

Related U.S. Application Data

(60) Provisional application No. 60/915,845, filed on May 3, 2007.

(51) Int. Cl.
C07D 213/82 (2006.01)
A61K 31/44 (2006.01)
(52) U.S. Cl. ......... 514/349; 514/350; 546/297; 546/298
(58) Field of Classification Search .................. None
See application file for complete search history.

(56) References Cited

U.S. PATENT DOCUMENTS
6,821,965 B1   11/2004  Brown et al.
2007/0265308 A1  11/2007  Nakai et al.

FOREIGN PATENT DOCUMENTS
EP   1 810 972    7/2007
WO   00 07980    2/2000
WO   2006 051826   5/2006
WO   2006 122154   11/2006
WO   2007 026950   3/2007

Primary Examiner — Zinna Northington Davis
(74) Attorney, Agent, or Firm — Oblon, Spivak, McClelland, Maier & Neustadt, L.L.P.

(57) ABSTRACT

A compound represented by the formula (I): wherein $R^1$ is lower alkyl, cycloalkyl or aromatic hydrocarbon ring, each of which is optionally substituted with one or more substituents; $R^2$ is hydrogen atom, halogen atom, lower alkyl, halo(lower) alkyl or lower alkoxy; and $R^3$ is (1) a group represented by the formula: wherein $R^4$ is lower alkyl, etc.; (2) a group represented by the formula: wherein $R^5$ is lower alkyl, etc.; (3) a group represented by the formula: wherein $R^6$ is lower alkyl, etc.; or (4) a group selected from halogen atom, carboxy, hydroxy and lower alkoxy, or a salt thereof.

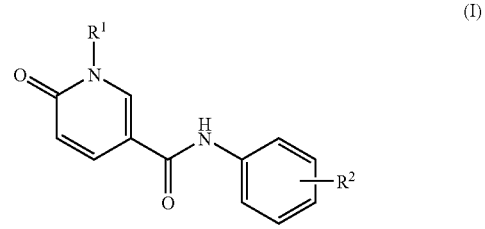

(I)

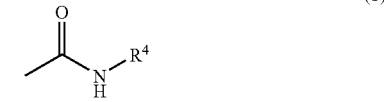

(1)

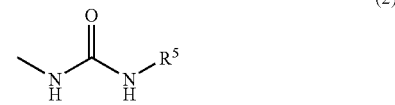

(2)

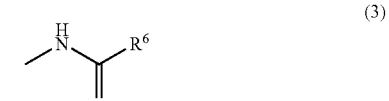

(3)

6 Claims, No Drawings

PYRIDONE DERIVATIVES AS P38α MAPK INHIBITORS

CONTINUING DATA

This application is a 371 of PCT/JP08/58689 filed May 2, 2008 which claims benefit of 60/915,845 filed May 3, 2007.

TECHNICAL FIELD

The present invention relates to a pyridone derivative compound and a salt thereof, which are useful for medicaments.

BACKGROUND OF THE INVENTION

Rheumatoid arthritis (RA) is a systemic inflammatory disease which causes mainly in the arthrosynovia. Today Methotrexate (MTX) is used generally as disease-modified anti-rheumatic drugs (DMARD), but the efficacy for inflammatory responses or arthritis mutilans is not enough. On the other hand, the biologics, which targeted cytokines (TNF, IL-1, IL-6), has been revealed recently its efficacy for RA, and it has been proved the importance of these cytokines in the manifestation of RA. In particular, the monoclonal TNF antibody Remicade and soluble TNF receptor fusion protein Enbrel, which inhibit the TNF function, are worthy of note because of the unprecedented efficacy not only for inflammatory response but for arthritis mutilans.

Though the fact above suggests importance of the treatment for RA in future, these biologics have fundamental drawbacks related to patient cost, efficacy of production, limitation of administration to hypodermal or intravenous injection, and so on. So, the anti-RA drugs in the next generation are expected to overcome these problems, that is to be an orally small-molecule drug, which blocks or modulates selectively the function of these cytokines. In particular p38α mitogen activated protein kinase (p38α MAPK) belongs to intracellular phosphorylation kinase participating in production and/or functional expression of the cytokine (TNF, IL-1, IL-6), and it is reported that p38α MAPK is activated in the arthrosynovia of RA patients thereby cytokines are produced excessively, so that p38α MAPK has been attracted as a target of anti-RA drug.

These anti-inflammatory agents or compounds having cytokine inhibitory activity have been described (WO98/22457, WO00/41698, WO00/43384, WO01/22965, WO02/07772, WO02/58695, WO03/041644, etc.) but pyridone derivatives having these activities are only described in WO2006/051826, WO2006/122154, WO2007/040208, WO2007/053610, WO2007053685, which does not include the compounds of the present invention, as far as we know.

DISCLOSURE OF THE INVENTION

The present invention relates to a pyridone derivative compound and a salt thereof, which are useful as medicaments; a pharmaceutical composition comprising, as an active ingredient, said pyridone derivative compound or a pharmaceutically acceptable salt thereof; a use of said pyridone derivative compound or a salt thereof as a medicament; and a method for using said pyridone derivative compound or a salt thereof for therapeutic purposes, which comprises administering said pyridone derivative compound or a salt thereof to a mammal.

The pyridone derivative compound and a salt thereof are inhibitors of cytokines' production or their transduction, and through inhibiting the p38α MAPK they possess pharmacological actions such as analgesic action, anti-inflammatory, anti arthritis mutilans action, or the like.

They are useful as an analgesic, in particular anti-RA agent, drug for pain and other conditions associated with inflammation, drug for Crohn's disease, drug for inflammatory bowel disease, drug for psoriasis, or the like.

The pyridone derivative compound or a salt thereof of the present invention is a compound shown by the following formula (I) (hereinafter also simply referred to as compound (I)):

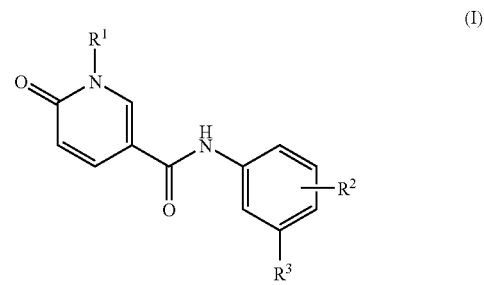

(I)

wherein
$R^1$ is lower alkyl, cycloalkyl or aromatic hydrocarbon ring, each of which is optionally substituted with one or more substituents;
$R^2$ is halogen atom, lower alkyl, halo(lower)alkyl or lower alkoxy; and
$R^3$ is
  (1) a group represented by the formula:

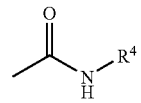

wherein
$R^4$ is lower alkyl, lower alkoxy, cycloalkyl, aromatic hetero ring, non-aromatic hetero ring or aromatic hydrocarbon ring, each of which is optionally substituted with one or more substituents;
  (2) a group represented by the formula:

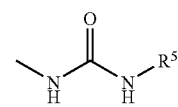

wherein
$R^5$ is lower alkyl, cycloalkyl, aromatic hydrocarbon ring, aromatic hetero ring or non-aromatic hetero ring, each of which is optionally substituted with one or more substituents;
  (3) a group represented by the formula:

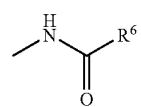

wherein
R[6] is lower alkyl, cycloalkyl, aromatic hydrocarbon ring or non-aromatic hetero ring, each of which is optionally substituted with one or more substituents; or
(4) a group selected from halogen atom, carboxy, hydroxy and lower alkoxy,
or a salt thereof.

BEST MODE FOR CARRYING OUT THE INVENTION

The compound of the present invention can be prepared by the following processes.

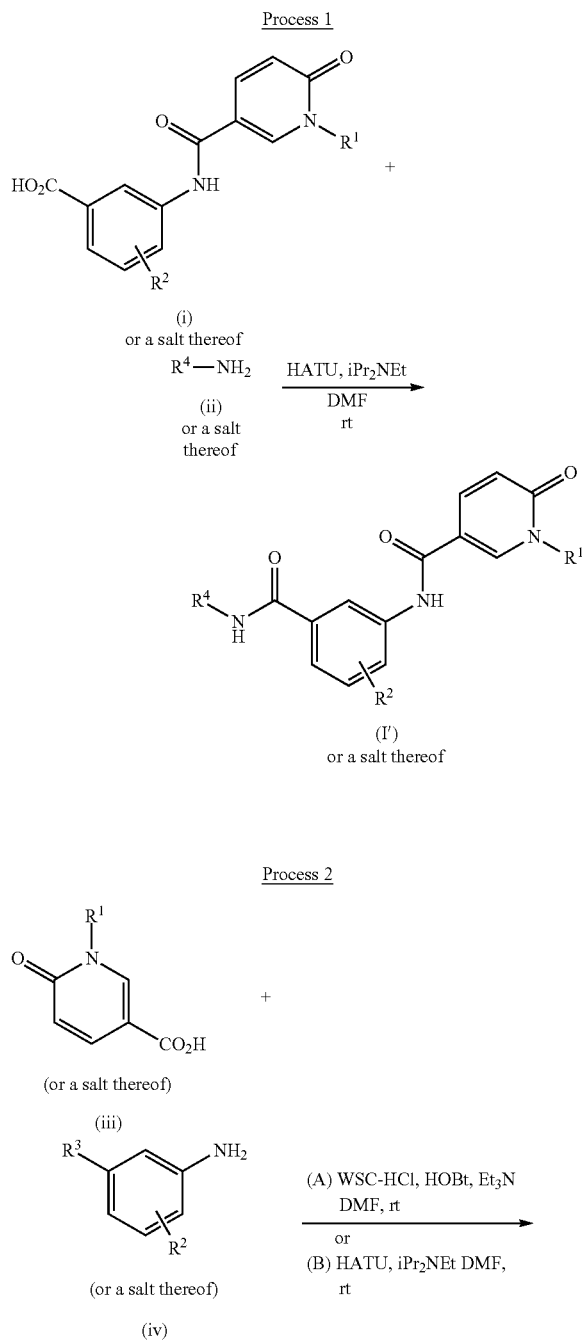

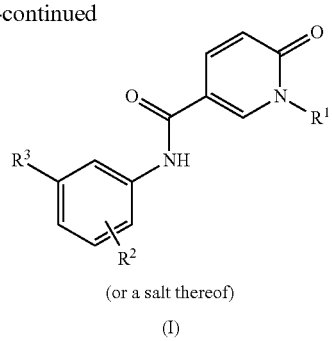

(or a salt thereof)
(I)

The symbols in the formulas in the above-mentioned Processes are as defined above.

In the above-mentioned schemes in Processes 1 and 2, "DMF" means N,N-dimethylformamide, "HATU" means N—[(dimethylamino)(3H-[1,2,3]triazolo[4,5-b]pyridin-3-yloxy)methylene]-N-methylmethanaminium hexafluorophosphate, "iPr$_2$NEt" means N-ethyl-N-isopropyl-2-propanamine, "WSC—HCl" means N-[3-(dimethylamino)propyl]-N'-ethylcarbodiimide hydrochloride, "HOBt" means 1-hydroxybenzotriazole, "Et$_3$N" means triethylamine, and "rt" means room temperature.

In the present specification, Process 1 is exemplified by Example 1, and Process 2 is exemplified by Examples 18, 20 and 25. However, the present invention is not restricted by these Examples.

In addition to the processes as mentioned above, the compound (I) and a salt thereof can be prepared, for example, according to the procedures as illustrated in Examples in the present specification or in a manner similar thereto.

The starting compounds can be prepared, for example, according to the procedures as illustrated in Preparations in the present specification or in a manner similar thereto.

The starting compound (iv) can also be prepared according to the manner disclosed in WO2004/071440.

It is to be noted that all solvated forms of the compound (I) (e.g., hydrates, ethanolates, etc.), all stereoisomers of the compound (I) (e.g., enantiomers, diastereomers, racemic compounds, etc.) and crystal forms of the compound (I) are also included within the scope of the present invention.

It is to be noted that radiolabelled derivatives of compound (I), which are suitable for biological studies, are also included within the scope of the present invention.

Suitable salts of the object compound (I) are conventional pharmaceutically acceptable ones and include metal salts such as alkali metal salts (e.g. sodium salt, potassium salt, etc.) and alkaline earth metal salts (e.g. calcium salt, magnesium salt, etc.), ammonium salts, organic base salts (e.g. trimethylamine salt, triethylamine salt, pyridine salt, picoline salt, dicyclohexylamine salt, N,N'-dibenzylethylenediamine salt, etc.), organic acid salts (e.g. acetate, trifluoroacetate, maleate, tartrate, fumarate, methanesulfonate, benzenesulfonate, formate, toluenesulfonate, etc.), inorganic acid salts (e.g. hydrochloride, hydrobromide, hydroiodide, sulfate, phosphate, etc.), a salt with an amino acid (e.g. arginine, aspartic acid, glutamic acid, etc.), etc.

All starting materials and product compounds may be salts. The compounds of above processes can be converted to salts according to a conventional method.

Hereinafter the definitions in the formula (I) are explained in detail.

(General Definitions)

Throughout the specification and claims, the term "lower" is intended to mean 1 to 6 carbon atom(s) unless otherwise indicated.

Examples of the "halogen atom" include fluorine atom, chlorine atom, bromine atom, iodine atom, etc.

Examples of the "lower alkyl" include straight or branched $(C_{1-6})$alkyl such as methyl, ethyl, propyl, isopropyl, butyl, isobutyl, tert-butyl, pentyl, hexyl, etc., of which preferred are $(C_{1-4})$alkyl such as methyl, ethyl, propyl, isopropyl, butyl, isobutyl, tert-butyl, etc.

Examples of the "halo(lower)alkyl" include groups in which the above-mentioned $(C_{1-6})$alkyl is substituted with one or more of the above-mentioned halogen atoms, of which preferred are halo$(C_{1-4})$alkyl such as fluoromethyl, difluoromethyl, trifluoromethyl, fluoroethyl, difluoroethyl, trifluoroethyl, tetrafluoroethyl, fluoropropyl, difluoropropyl, trifluoropropyl, tetrafluoropropyl, fluorobutyl, difluorobutyl, trifluorobutyl, tetrafluorobutyl, chloromethyl, dichloromethyl, trichloromethyl, chloroethyl, dichloroethyl, trichloroethyl, tetrachloroethyl, chloropropyl, dichloropropyl, trichloropropyl, tetrachloropropyl, chlorobutyl, dichlorobutyl, trichlorobutyl, tetrachlorobutyl, bromomethyl, dibromomethyl, tribromomethyl, bromoethyl, dibromoethyl, tribromoethyl, tetrabromoethyl, bromopropyl, dibromopropyl, tribromopropyl, tetrabromopropyl, bromobutyl, dibromobutyl, tribromobutyl, tetrabromobutyl, chlorofluoromethyl, bromochloroethyl, etc.

Examples of the "lower alkoxy" include straight or branched $(C_{1-6})$alkoxy such as methoxy, ethoxy, propoxy, isopropoxy, butoxy, isobutoxy, tert-butoxy, pentyloxy, hexyloxy, etc., in which the preferred one are $(C_{1-4})$alkoxy such as methoxy, ethoxy, propoxy, isopropoxy, butoxy, isobutoxy, tert-butoxy, etc.

Examples of the "cycloalkyl" include $(C_{3-7})$cycloalkyl such as cyclopropyl, cyclobutyl, cyclopentyl, cyclohexyl, cycloheptyl etc., of which preferred are $(C_{3-6})$cycloalkyl such as cyclopropyl, cyclobutyl, cyclopentyl, cyclohexyl, etc.

Examples of the "aromatic hydrocarbon ring" include $(C_{6-16})$ aryl such as phenyl, naphthyl, anthryl, pyrenyl, pentalenyl, indenyl, phenanthryl, azulenyl, heptalenyl, octalenyl, etc., in which preferred are $(C_{6-14})$aryl such as phenyl, naphthyl, etc.

Examples of the "aromatic hetero ring" include aromatic hetero ring having 5 to 14 ring atoms and π electrons shared in a cyclic array and containing 1 to 4 heteroatoms selected from a nitrogen atom, an oxygen atom and a sulfur atom besides carbon atoms. Suitable examples of the "aromatic hetero ring" include 5- to 14-membered hetero ring such as thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, isoxazolyl, 1,2,4-oxadiazolyl, 1,3,4-oxadiazolyl, 1,2,5-oxadiazolyl, etc., of which preferred are 5- or 6-membered hetero ring such as thienyl, furyl, pyrrolyl, imidazolyl, pyrazolyl, pyridyl, pyrazinyl, pyrimidinyl, tetrazolyl, oxazolyl, thiazolyl, isoxazolyl, 1,3,4-oxadiazolyl, etc.

Examples of the "non-aromatic hetero ring" include non-aromatic hetero ring having 5 to 14 ring atoms and containing 1 to 3 heteroatoms selected from nitrogen atom, oxygen atom and sulfur atom besides carbon atoms. Suitable examples of "non-aromatic hetero ring" include 5- to 14-membered hetero ring such as pyrrolidinyl, pyrazolidinyl, imidazolidinyl, isoxazolidinyl, isothiazolidinyl, piperidyl (e.g., piperidino etc.), piperazinyl, morpholinyl (e.g., morpholino etc.), thiomorpholinyl (e.g., thiomorpholino etc.), tetrahydrofuranyl, tetrahydropyranyl, tetrahydrothienyl, 1,2,3,4-tetrahydroquinolyl, etc., of which preferred are 5- or 6-membered hetero ring such as pyrrolidinyl, pyrazolidinyl, imidazolidinyl, isoxazolidinyl, isothiazolidinyl, piperidyl (e.g., piperidino etc.), piperazinyl, morpholinyl (e.g., morpholino etc.), thiomorpholinyl (e.g., thiomorpholino etc.), tetrahydrofuranyl, tetrahydrothienyl, etc.

(Definition of $R^1$)

In the compound (I), $R^1$ is lower alkyl, cycloalkyl or aromatic hydrocarbon ring, each of which is optionally substituted with one or more suitable substituents.

Suitable examples of the "lower alkyl" for $R^1$ include $(C_{1-6})$alkyl as exemplified in the "General Definitions", of which preferred are $(C_{1-4})$alkyl such as ethyl, tert-butyl, etc.

Suitable examples of the "cycloalkyl" for $R^1$ include $(C_{3-7})$cycloalkyl as exemplified in the "General Definitions", of which preferred are $(C_{3-6})$cycloalkyl such as cyclohexyl, etc.

Suitable examples of the "aromatic hydrocarbon ring" for $R^1$ includes $(C_{6-16})$ aryl as exemplified in the "General Definitions", of which preferred are $(C_{6-14})$ aryl such as phenyl, etc.

Each of the "lower alkyl", "cycloalkyl" and "aromatic hydrocarbon ring" for $R^1$ is optionally substituted by one or more substituents. Suitable examples of the "substituent" include:

(i) halogen atom [e.g., fluorine atom, chlorine atom, etc.];

(ii) $(C_{1-6})$ alkyl [e.g., $(C_{1-4})$ alkyl such as methyl, etc.];

(iii) $(C_{6-16})$ aryl [e.g., $(C_{6-14})$ aryl such as phenyl, etc.];

(iv) $(C_{1-6})$alkoxy [e.g., $(C_{1-4})$ alkoxy such as methoxy, etc.];

(v) hydroxy;

(vi) cyano;

(vii) $(C_{1-6})$ alkylamino [e.g., $(C_{1-4})$ alkylamino such as methylamino etc.];

(viii) $(C_{3-7})$ cycloalkyl [e.g., $(C_{3-6})$ cycloalkyl such as cyclopropyl, etc.], etc.

The number of the substituents is generally 1 to 4, preferably 1 to 3.

In a preferred embodiment, $R^1$ is (1) $(C_{1-6})$ alkyl optionally substituted with one $(C_{6-16})$aryl, (2) $(C_{3-7})$cycloalkyl, or (3) $(C_{6-16})$ aryl optionally substituted with 1 to 3 substituents selected from halogen atom, $(C_{1-6})$ alkyl and $(C_{6-16})$ aryl.

(Definition of $R^2$)

In the compound (I), $R^2$ is halogen atom, lower alkyl, halo(lower)alkyl or lower alkoxy.

Suitable examples of the "halogen atom" for $R^2$ include those exemplified in the "General Definitions", of which preferred are chlorine atom, bromine atom, etc.

Suitable examples of the "lower alkyl" for $R^2$ include $(C_{1-6})$alkyl as exemplified in the "General Definitions", of which preferred are $(C_{1-4})$alkyl such as methyl, etc.

Suitable examples of the "halo(lower)alkyl" for $R^2$ include those exemplified in the "General Definitions", of which preferred are fluoromethyl, difluoromethyl, trifluoromethyl, etc.

Suitable examples of the "lower alkoxy" for $R^2$ include $(C_{1-6})$alkoxy as exemplified in the "General Definitions", of which preferred are $(C_{1-4})$ alkoxy such as methoxy, ethoxy, isopropoxy, etc.

In a preferred embodiment, $R^2$ is halogen atom or $(C_{1-6})$ alkyl.

(Definitions of $R^3$, $R^4$, $R^5$ and $R^6$)
In the compound (I), $R^3$ is
(1) a group represented by the formula:

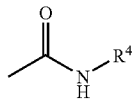

wherein
$R^4$ is lower alkyl, lower alkoxy, cycloalkyl, aromatic hetero ring, non-aromatic hetero ring or aromatic hydrocarbon ring, each of which is optionally substituted with one or more substituents;
(2) a group represented by the formula:

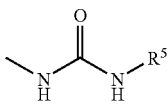

wherein
$R^5$ is lower alkyl, cycloalkyl, aromatic hydrocarbon ring, aromatic hetero ring or non-aromatic hetero ring, each of which is optionally substituted with one or more substituents;
(3) a group represented by the formula:

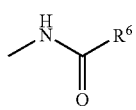

wherein
$R^6$ is lower alkyl, cycloalkyl, aromatic hydrocarbon ring or non-aromatic hetero ring, each of which is optionally substituted with one or more substituents; or
(4) a group selected from halogen atom, carboxy, hydroxy and lower alkoxy.
(1) Suitable examples of the "lower alkyl" for $R^4$ include $(C_{1-6})$alkyl as exemplified in the "General Definitions", of which preferred are $(C_{1-4})$alkyl such as methyl, ethyl, isopropyl, etc.

Suitable examples of the "lower alkoxy" for $R^4$ include $(C_{1-6})$alkoxy as exemplified in the "General Definitions", of which preferred are $(C_{1-4})$alkoxy such as methoxy, etc.

Suitable examples of the "cycloalkyl" for $R^4$ include $(C_{3-7})$cycloalkyl as exemplified in the "General Definitions", of which preferred are $(C_{3-6})$cycloalkyl such as cyclopropyl, etc.

Suitable examples of the "aromatic hetero ring" for $R^4$ include "5- to 14-membered aromatic hetero ring" as exemplified in the "General Definitions", of which preferred are 5- or 6-membered aromatic hetero ring such as isoxazolyl, pyridyl, pyrazolyl, 1,3,4-oxadiazolyl, etc.

Suitable examples of the "non-aromatic hetero ring" for $R^4$ include "5- to 14-membered non-aromatic hetero ring" as exemplified in the "General Definitions", of which preferred are 5- or 6-membered hetero ring such as pyrrolidinyl, piperidyl, tetrahydropyranyl, etc.

Suitable examples of the "aromatic hydrocarbon ring" for $R^4$ include $(C_{6-16})$ aryl as exemplified in the "General Definitions", of which preferred are $(C_{6-14})$ aryl such as phenyl, etc.

Each of the "lower alkyl", "lower alkoxy", "cycloalkyl", "aromatic hetero ring", "non-aromatic hetero ring" and "aromatic hydrocarbon ring" for $R^4$ is optionally substituted with one or more substituents. Examples of the "substituent" include:
(i) $(C_{1-6})$ alkyl [e.g., $(C_1-4)$ alkyl such as methyl, etc.];
(ii) $(C_{3-7})$ cycloalkyl [e.g., $(C_{3-6})$ cycloalkyl such as cyclopropyl, etc.];
(iii) $(C_{6-16})$ aryl [e.g., $(C_{6-14})$ aryl such as phenyl, etc.];
(iv) $(C_{1-6})$ alkylamino [e.g., $(C_{1-3})$ alkylamino such as methylamino, etc.];
(v) halo$(C_{1-6})$alkyl [e.g., halo$(C_{1-3})$alkyl such as trifluoromethyl, etc.];
(vi) halogen atom [e.g., fluorine atom, etc.], etc.
(vii) non-aromatic hetero ring [e.g., morpholino, etc.];
The number of the substituents is generally 1 to 4, preferably 1 to 3.
(2) Suitable examples of the "lower alkyl" for $R^5$ include $(C_{1-6})$alkyl as exemplified in the "General Definitions", of which preferred are $(C_{1-4})$ alkyl such as methyl, ethyl, etc.

Suitable examples of the "cycloalkyl" for $R^5$ include $(C_{3-7})$cycloalkyl as exemplified in the "General Definitions", of which preferred are $(C_{3-6})$cycloalkyl such as cyclopropyl, cyclopentyl, etc.

Suitable examples of the "aromatic hydrocarbon ring" for $R^5$ include $(C_{6-16})$ aryl as exemplified in the "General Definitions", of which preferred are $(C_{6-14})$aryl such as phenyl, naphthyl, etc.

Suitable examples of the "aromatic hetero ring" for $R^5$ include "5- to 14-membered aromatic hetero ring" as exemplified in the "General Definitions", of which preferred are 5- or 6-membered hetero ring such as isoxazolyl, pyridyl, pyrazolyl, 1,3,4-oxadiazolyl, etc.

Suitable examples of the "non-aromatic hetero ring" for $R^5$ include "5- to 14-membered non-aromatic hetero ring" as exemplified in the "General Definitions", of which preferred are 5- or 6-membered hetero ring such as pyrrolidinyl, piperidyl, tetrahydropyranyl, etc.

Each of the "lower alkyl", "cycloalkyl", "aromatic hydrocarbon ring", "aromatic hetero ring" and "non-aromatic hetero ring" for $R^5$ is optionally substituted with one or more substituents. Suitable examples of the "substituent" include:
(i) $(C_{1-6})$alkyl [e.g., $(C_{1-4})$alkyl such as methyl, tert-butyl, etc.];
(ii) $(C_{3-7})$ cycloalkyl [e.g., $(C_{3-6})$ cycloalkyl such as cyclopropyl, etc.];
(iii) $(C_{6-16})$aryl [e.g., $(C_{6-14})$ aryl such as phenyl, etc.] which is optionally substituted with $(C_{1-6})$ alkyl [e.g., $(C_{1-6})$ alkyl such as methyl, etc.];
(iv) $(C_{1-6})$ alkylamino [e.g., $(C_{1-3})$ alkylamino such as methylamino, etc.];
(v) halo$(C_{1-6})$ alkyl [e.g., halo$(C_{1-3})$ alkyl such as trifluoromethyl, etc.];
(vi) halogen atom [e.g., fluorine atom, etc.];
(vii) non-aromatic hetero ring [e.g., morpholino, etc.], etc.
The number of the substituents is generally 1 to 4, preferably 1 to 3.
(3) Suitable examples of the "lower alkyl" for $R^6$ include $(C_{1-6})$alkyl as exemplified in the "General Definitions", of which preferred are $(C_{1-4})$alkyl such as methyl, ethyl, isopropyl, tert-butyl, etc.

Suitable examples of the "cycloalkyl" for $R^6$ include $(C_{3-7})$cycloalkyl as exemplified in the "General Definitions", of which preferred are $(C_{3-6})$cycloalkyl such as cyclopropyl, etc.

Suitable examples of the "aromatic hydrocarbon ring" for $R^6$ include $(C_{6-16})$aryl as exemplified in the "General Definitions", of which preferred are $(C_{6-14})$aryl such as phenyl, naphthyl, etc.

Suitable examples of the "non-aromatic hetero ring" for $R^6$ include "5- to 14-membered non-aromatic hetero ring" as exemplified in the "General Definitions", of which preferred are 5- or 6-membered hetero ring such as pyrrolidinyl, piperidyl, tetrahydropyranyl, etc.

Each of the "lower alkyl", "cycloalkyl", "aromatic hydrocarbon ring" and "non-aromatic hetero ring" for $R^6$ is optionally substituted with one or more substituents. Suitable examples of the "substituent" include:

(i) $(C_{1-6})$ alkyl [e.g., $(C_{1-4})$ alkyl such as methyl, etc.];

(ii) $(C_{3-7})$ cycloalkyl [e.g., $(C_{3-6})$ cycloalkyl such as cyclopropyl, etc.];

(iii) $(C_{6-16})$ aryl [e.g., $(C_{6-14})$aryl such as phenyl, etc.];

(iv) $(C_{1-6})$ alkylamino [e.g., $(C_{1-3})$ alkylamino such as methylamino, etc.];

(v) halo$(C_{1-6})$ alkyl [e.g., halo$(C_{1-3})$ alkyl such as trifluoromethyl, etc.];

(vi) halogen atom [e.g., fluorine atom, etc.];

(vii) non-aromatic hetero ring [e.g., morpholino, etc.], etc.

The number of the substituents is generally 1 to 4, preferably 1 to 3.

(4) Suitable examples of the "halogen atom" for $R^3$ include halogen atom as exemplified in the "General Definitions", of which preferred are fluorine atom, chlorine atom, bromine atom, etc.

Suitable examples of the "lower alkoxy" for $R^3$ include $(C_{1-6})$alkoxy as exemplified in the "General Definitions", of which preferred are $(C_{1-4})$alkoxy such as methoxy, ethoxy, etc.

In a preferred embodiment, $R^3$ is (1) a group represented by the formula:

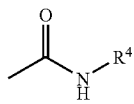

wherein $R^4$ is $(C_{1-6})$alkoxy, $(C_{3-7})$ cycloalkyl, 5- to 14-membered aromatic hetero ring or $(C_{6-16})$aryl, each of which is optionally substituted with 1 to 3 substituents selected from $(C_{1-6})$ alkyl, $(C_{3-7})$cycloalkyl and $(C_{6-16})$ aryl, (2) a group represented by the formula:

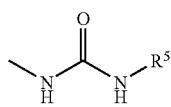

wherein $R^5$ is $(C_{3-7})$cycloalkyl, $(C_{6-16})$aryl or 5- to 14-membered aromatic hetero ring, each of which is optionally substituted with 1 to 3 substituents selected from $(C_{1-6})$alkyl and $(C_{6-16})$aryl which is optionally substituted with $(C_{1-6})$alkyl, or (3) a group represented by the formula:

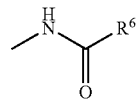

wherein $R^6$ is $(C_{3-7})$ cycloalkyl

A preferred embodiment of compound (I) is $R^1$ is lower alkyl, cycloalkyl or aromatic hydrocarbon ring, each of which is optionally substituted with one or more substituents;

$R^2$ is halogen atom or lower alkyl; and $R^3$ is (1) a group represented by the formula:

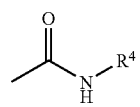

wherein $R^4$ is lower alkoxy, cycloalkyl, aromatic hetero ring or aromatic hydrocarbon ring, each of which is optionally substituted with one or more substituents, (2) a group represented by the formula:

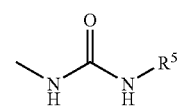

wherein $R^5$ is cycloalkyl, aromatic hydrocarbon ring or aromatic hetero ring, each of which is optionally substituted with one or more substituents; or (3) a group represented by the formula:

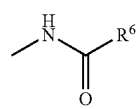

wherein $R^6$ is cycloalkyl, which is optionally substituted with one or more substituents, or a salt thereof.

And more preferred embodiment of compound (I) is $R^1$ is (1) $(C_{1-6})$ alkyl optionally substituted with one $(C_{6-16})$ aryl, (2) $(C_{3-7})$ cycloalkyl, or (3) $(C_{6-16})$aryl optionally substituted with 1 to 3 substituents selected from halogen atom, $(C_{1-6})$alkyl and $(C_{6-16})$ aryl;

$R^2$ is halogen atom or $(C_{1-6})$alkyl, and

R³ is
(1) a group represented by the formula:

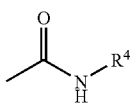

wherein
R⁴ is $(C_{1-6})$alkoxy, $(C_{3-7})$ cycloalkyl, 5- to 14-membered aromatic hetero ring or $(C_{6-16})$aryl, each of which is optionally substituted with 1 to 3 substituents selected from $(C_{1-6})$ alkyl, $(C_{3-7})$ cycloalkyl and $(C_{6-16})$ aryl,
(2) a group represented by the formula:

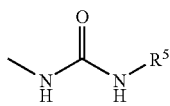

wherein
R⁵ is $(C_{3-7})$ cycloalkyl, $(C_{6-16})$ aryl or 5- to 14-membered aromatic hetero ring, each of which is optionally substituted with 1 to 3 substituents selected from $(C_{1-6})$ alkyl and $(C_{6-16})$ aryl which is optionally substituted with $(C_{1-6})$alkyl, or
(3) a group represented by the formula:

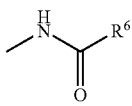

wherein
R⁶ is $(C_{3-7})$cycloalkyl,
or a salt thereof.

Specific examples of the preferred compound of the present invention may be exemplified by Examples below.

In order to show the usefulness of the compound (I) of the present invention, the pharmacological test results of the representative compounds of the present invention are shown in the following.

Test 1: Inhibition of TNF-α Production in THP-1 Cells

[I] Test Method

THP-1 cells, a human monocytic cell line, were maintained in RPMI 1640 (Sigma R8758) supplemented with penicillin (50 U/mL), streptomycin (50 μg/mL) and 10% fetal bovine serum (Moregate BioTech.) at 37° C., 5% $CO_2$ in a humidified incubator. Initial stock solutions of test compounds were made in DMSO. All cells, reagents and test compounds were diluted into culture media. THP-1 cells ($1 \times 10^5$ cells/well final) and lipopolysaccharide (LPS; 10 μg/mL final; Sigma L-4005, from *E. coli* serotype 0.55:B5) were added to 96 well polypropylene culture plates (Sumilon, MS-8196F5; sterile) containing test compound or 0.1% DMSO vehicle. The cell mixture was incubated for 20 hr in a humidified incubator at 37° C., 5% $CO_2$. The culture supernatants were harvested and TNF-α levels from LPS stimulated cells in the presence of 100 nM test compound was calculated compared with control cells stimulated in the presence of 0.1% DMSO.

[II] Test Compounds

N-{2-Chloro-5-[(cyclopropylamino)carbonyl]phenyl}-1-(2,6-dichlorophenyl)-6-oxo-1,6-dihydro-3-pyridinecarboxamide (Example 1)

N-{2-Chloro-5-[(methoxyamino)carbonyl]phenyl}-1-(2,6-dichlorophenyl)-6-oxo-1,6-dihydro-3-pyridinecarboxamide (Example 2)

N-{2-Chloro-5-[(isoxazol-3-ylamino)carbonyl]phenyl}-1-(2,6-dichlorophenyl)-6-oxo-1,6-dihydro-3-pyridinecarboxamide (Example 3)

N-{2-Chloro-5-[(1-methyl-1H-pyrazol-3-ylamino)carbonyl]phenyl}-1-(2,6-dichlorophenyl)-6-oxo-1,6-dihydro-3-pyridinecarboxamide (Example 5)

N-{2-Chloro-5-[(1-methyl-1H-pyrazol-5-ylamino)carbonyl]phenyl}-1-(2,6-dichlorophenyl)-6-oxo-1,6-dihydro-3-pyridinecarboxamide (Example 6)

N-{2-Bromo-5-[(cyclopropylamino)carbonyl]phenyl}-1-(2,6-difluorophenyl)-6-oxo-1,6-dihydro-3-pyridinecarboxamide (Example 15)

N-{2-Chloro-5-[(cyclopropylamino)carbonyl]phenyl}-1-(2-chloro-6-fluorophenyl)-6-oxo-1,6-dihydro-3-pyridinecarboxamide (Example 16)

N-{2-Chloro-5-[(cyclopropylamino)carbonyl]phenyl}-1-(2,3-difluorophenyl)-6-oxo-1,6-dihydro-3-pyridinecarboxamide (Example 17)

N-{5-[(Cyclopropylamino)carbonyl]-2-methylphenyl}-1-(2,6-dichlorophenyl)-6-oxo-1,6-dihydro-3-pyridinecarboxamide (Example 18)

N-{5-[(Cyclopropylamino)carbonyl]-2-methylphenyl}-1-tert-butyl-6-oxo-1,6-dihydro-3-pyridinecarboxamide (Example 20)

N-{5-[(Cyclopropylamino)carbonyl]-2-methylphenyl}-1-(2,6-difluorolphenyl)-6-oxo-1,6-dihydro-3-pyridinecarboxamide (Example 22)

N-{5-[(Cyclopropylamino)carbonyl]-2-methylphenyl}-1-(1-phenylethyl)-6-oxo-1,6-dihydro-3-pyridinecarboxamide (Example 24)

N-{5-[(Cyclopropylcarbonyl)amino]-2-methylphenyl}-1-(2,6-dichlorophenyl)-6-oxo-1,6-dihydro-3-pyridinecarboxamide (Example 25)

N-[5-[({[3-tert-butyl-1-(4-methylphenyl)-1H-pyrazol-5-yl]amino]carbonyl)amino]-2-methylphenyl}-1-(2,6-dichlorophenyl)-6-oxo-1,6-dihydro-3-pyridinecarboxamide (Example 26)

[III] Test Results

TABLE 1

Inhibition of TNF-α production in THP-1 cells at 100 nM

| Test compounds (Example Nos.) | % inhibition of control |
|---|---|
| Example 1 | 77 |
| Example 2 | 84 |
| Example 3 | 94 |
| Example 5 | 75 |
| Example 6 | 82 |
| Example 15 | 69 |
| Example 16 | 72 |
| Example 17 | 75 |
| Example 18 | 78 |
| Example 20 | 85 |
| Example 22 | 97 |
| Example 24 | 83 |
| Example 25 | 70 |
| Example 26 | 68 |

Test 2: Inhibition of Hind Paw Swelling in Adjuvant-Induced Arthritis Rats

[I] Test Method

Arthritis was induced by injection of 0.5 mg of *Mycobacterium tuberculosis* (Difco Laboratories, Detroit, Mich.) in 50 μL of liquid paraffin into the right hind footpad of female Lewis rats aged 7 weeks (day 0). Normal untreated rats were used as negative controls. Animals were randomized and grouped (n≧5) for drug treatment based on an increase of left hind paw volume and body weight on day 15. Test compounds were suspended in vehicle (0.5% methylcellulose) and orally administered once a day from days 15 to 24. The volume of the left hind paw was measured on day 25 by a water displacement method using a plethymometer for rats (MK-550; Muromachi Kikai Co., Ltd., Tokyo, Japan).

The compound (I) and a salt thereof of the present invention are useful as inhibitors of cytokines' production or their transduction, and through inhibiting the p38α MAPK they possess pharmacological actions such as analgesic action, anti-inflammatory, anti arthritis mutilans action, or the like, and for the prevention and/or the treatment of pain, rheumatoid arthritis, other conditions associated with inflammation, Crohn's disease, inflammatory bowel disease, psoriasis, or the like.

The pharmaceutical composition of the present invention can be used in the form of a pharmaceutical preparation, for example, in a solid, semisolid or liquid form, which contains the compound (I) or a pharmaceutically acceptable salt thereof as an active ingredient in admixture with an organic or inorganic carrier or excipient suitable for rectal, pulmonary (nasal or buccal inhalation), nasal, ocular, external (topical), oral or parenteral (including subcutaneous, intravenous and intramuscular) administrations or insufflations. The active ingredient may be compounded, for example, with the usual non-toxic, pharmaceutically acceptable carriers for tablets, pellets, troches, capsules, suppositories, creams, ointments, aerosols, powders for insufflation, solutions, emulsions, suspensions, and any other form suitable for use. In addition, auxiliary, stabilizing agents, thickening agents, coloring agents and perfumes may be used where necessary. The compound (I) or a pharmaceutically acceptable salt thereof is included in a pharmaceutical composition in an amount sufficient to produce the desired aforesaid pharmaceutical effect upon the process or condition of diseases.

For applying the composition to a mammal (e.g., human being, mouse, rat, swine, dog, cat, horse, bovine, etc., especially human being), it is preferable to apply the composition by intravenous, intramuscular, pulmonary or oral administration, or insufflation. While the dosage of therapeutically effective amount of the compound (I) varies depending on the age and condition of each individual patient to be treated, in the case of intravenous administration, a daily dose of 0.01-100 mg of the compound (I) per kg weight of a mammal, in the case of intramuscular administration, a daily dose of 0.1-100 mg of the compound (I) per kg weight of a mammal, and in case of oral administration, a daily dose of 0.5-100 mg of the compound (I) per kg weight of a mammal is generally given for the prevention and/or treatment of the aforesaid diseases.

Hereinafter the reactions for preparing the compound [I] of the invention are explained in more detail with referring to the Preparations and Examples. However, the Preparations and Examples are given only for the purpose of illustration of the present invention, and the present invention should not be restricted by the Preparations and Examples in any way.

The abbreviations, symbols and term used in the Preparations and Examples have the following meanings.

$CH_2Cl_2$: dichloromethane
EtOAc: ethyl acetate
MeOH: methanol
DMF: N,N-dimethylformamide
$Et_3N$: triethylamine
$iPr_2NEt$: N-ethyl-N-isopropyl-2-propanamine
IPE: diisopropyl ether
THF: tetrahydrofuran
HOBt: 1-hydroxybenzotriazole
HATU: N-[(dimethylamino)(3H-[1,2,3]triazolo[4,5-b]pyridin-3-yloxy)methylene]-N-methylmethanaminium hexafluorophosphate
Pd/C: palladium on carbon
min: minute(s)
hr: hour(s)
HCl: hydrochloric acid
NaOH: sodium hydroxide
WSC—HCl: N-[3-(dimethylamino)propyl]-N'-ethylcarbodiimide hydrochloride
$MgSO_4$: magnesium sulfate
$NaHCO_3$: sodium hydrogen carbonate
DMSO: dimethyl sulfoxide Preparation 1

To a solution of (2,6-dichlorophenyl)amine (12.8 g) in THF (73 mL) was added an 1 M THF solution of lithium 1,1,1,3,3,3-hexamethyldisilazan-2-ide (79.8 mL) at 0° C. under a nitrogen atmosphere, and the mixture was stirred at the same temperature for 30 min. To this solution was added a solution of dimethyl (2E,4Z)-4-(methoxymethylene)-2-pentenedioate (14.52 g) in THF (35 ml) at once, and the resulting mixture was stirred at 0° C. for 3 hr. The reaction mixture was diluted with EtOAc (150 mL) and washed with a mixture of 1 M HCl (200 mL) and brine (150 mL), saturated aqueous $NaHCO_3$ (150 mL) and brine successively, dried over $MgSO_4$ and filtered. The filtrate was evaporated in vacuo, and the residue was triturated with a mixture of EtOAc and hexane (1:2) and collected by filtration to give dimethyl (2E,4Z)-4-{[(2,6-dichlorophenyl)amino]methylene}-2-pentenedioate (9.28 g). The filtrate was evaporated in vacuo and the residue was purified by silica gel (200 g) column chromatography eluting with EtOAc-hexane (1:2) followed by triturating the isolated material with EtOAc-hexane (1:2) to afford dimethyl (2E,4Z)-4-{[(2,6-dichlorophenyl)amino]methylene}-2-pentenedioate (1.30 g).

Mass ESI (+) 330 (M+H)

$^1$H-NMR (DMSO-$d_6$) δ 3.62 (3H, s), 3.80 (3H, s), 6.20 (1H, d, J=15.7 Hz), 7.29-7.37 (1H, m), 7.60 (2H, d, J=8.14 Hz), 8.00 (1H, d, J=13.3 Hz), 10.27 (1H, d, J=13.3 Hz)

Preparation 2

Dimethyl (2E,4Z)-4-{[(2,6-dimethyl-4-fluorophenyl)amino]methylene}-2-pentenedioate was obtained according to a similar manner to Preparation 1.

Mass ESI (+) 330 (M+Na)

$^1$H-NMR (CDCl$_3$) δ 2.27 (6H, s), 3.73 (3H, s), 3.86 (3H, s), 6.12 (1H, d, J=15.72 Hz), 6.81 (1H, d, J=8.84 Hz), 7.19 (1H, d, J=13.23 Hz), 7.39 (1H, d, J=15.68 Hz), 10.08 (1H, d, J=13.20 Hz)

Preparation 3

Dimethyl (2E,4Z)-4-{[(2-chloro-6-fluorophenyl)amino]methylene}-2-pentenedioate was obtained according to a similar manner to Preparation 1.

Mass ESI (+) 336 (M+Na)

$^1$H-NMR (CDCl$_3$) δ 3.76 (3H, s), 3.91 (3H, s), 6.21 (1H, d, J=15.88 Hz), 6.98-7.23 (3H, m), 7.44 (1H, d, J=15.82 Hz), 7.97 (1H, d, J=12.86 Hz), 10.96 (1H, d, J=12.78 Hz)

Preparation 4

Dimethyl (2E,4Z)-4-[(tert-butylamino)methylene]-2-pentenedioate was obtained according to a similar manner to Preparation 1.

Mass ESI (+) 264 (M+Na)

$^1$H-NMR (CDCl$_3$) δ 1.36 (9H, s), 3.73 (3H, s), 3.78 (3H, s), 6.02 (1H, d, J=15.6 Hz), 7.35 (1H, d, J=14.1 Hz), 7.40 (1H, d, J=15.6 Hz), 9.23 (1H, br d)

Preparation 5

Dimethyl (2E,4Z)-4-{[(2,6-dimethylphenyl)amino]methylene}-2-pentenedioate was obtained according to a similar manner to Preparation 1.

Mass ESI (+) 312 (M+Na)

$^1$H-NMR (CDCl$_3$) δ 2.23 (6H, s), 3.73 (3H, s), 3.86 (3H, s), 6.12 (1H, d, J=15.7 Hz), 7.02-7.16 (3H, m), 7.29 (1H, d, J=13.9 Hz), 7.41 (1H, d, J=15.7 Hz), 10.24 (1H, d, J=13.0 Hz)

Preparation 6

Dimethyl (2E,4Z)-4-{[(2,6-difluorophenyl)amino]methylene}-2-pentenedioate was obtained according to a similar manner to Preparation 1.

Mass ESI (+) 320 (M+Na)

$^1$H-NMR (CDCl$_3$) δ 3.76 (3H, s), 3.94 (3H, s), 6.20 (1H, d, J=15.72 Hz), 6.76-7.04 (3H, m), 7.44 (1H, d, J=15.80 Hz), 7.96 (1H, d, J=12.86 Hz), 10.79 (1H, d, J=11.68 Hz)

Preparation 7

To a solution of dimethyl (2E,4Z)-4-{[(2,6-dichlorophenyl)amino]methylene}-2-pentenedioate (7.3 g) in MeOH (73 mL) was added 28% sodium methoxide in MeOH (4.3 mL). The mixture was refluxed for 8 hr under a nitrogen atmosphere. The reaction mixture was cooled to room temperature and poured into 1 M HCl (140 ml) at 0° C. The resulting mixture was extracted with EtOAc (70 mL×2). The combined extracts were washed with saturated aqueous NaHCO$_3$ (100 mL) and brine, dried over MgSO$_4$ and filtered. The filtrate was evaporated in vacuo, and the residue was triturated with a mixture of EtOAc and hexane (1:3) to provide methyl 1-(2,6-dichlorophenyl)-6-oxo-1,6-dihydro-3-pyridinecarboxylate (4.3 g).

Mass ESI (+) 300 (M+H)

$^1$H-NMR (CDCl$_3$) δ 3.87 (3H, s), 6.68 (1H, d, J=10.28 Hz), 7.39 (1H, dd, J=9.42 and 5.84 Hz), 7.49-7.53 (2H, m), 7.94-8.01 (2H, m)

Preparation 8

Methyl 1-(2,6-dimethyl-4-fluorophenyl)-6-oxo-1,6-dihydro-3-pyridinecarboxylate was obtained according to a similar manner to Preparation 7.

Mass ESI (+) 298 (M+Na)

$^1$H-NMR (CDCl$_3$) δ 2.08 (6H, s), 3.86 (3H, s), 6.68 (1H, dd, J=8.32 and 2.44 Hz), 6.90 (2H, d, J=8.80 Hz), 7.98 (2H, dd, J=8.40 and 2.48 Hz)

Preparation 9

Methyl 1-(2-chloro-6-fluorophenyl)-6-oxo-1,6-dihydro-3-pyridinecarboxylate was obtained according to a similar manner to Preparation 7.

Mass ESI (+) 282 (M+H)

$^1$H-NMR (CDCl$_3$) δ 3.87 (3H, s), 6.68 (1H, d, J=9.38 Hz), 7.02-7.25 (1H, m), 7.40-7.46 (2H, m), 7.93-8.04 (2H, m)

Preparation 10

Methyl 1-(2,6-difluorophenyl)-6-oxo-1,6-dihydro-3-pyridinecarboxylate was obtained according to a similar manner to Preparation 7.

Mass ESI (+) 288 (M+Na)

$^1$H-NMR (CDCl$_3$) δ 3.87 (3H, s), 6.67 (1H, d, J=9.84 Hz), 7.08-7.13 (2H, m), 7.44-7.48 (1H, m), 7.95 (1H, dd, J=9.80 and 2.52 Hz), 8.09 (1H, s)

Preparation 11

To a solution of dimethyl (2E,4Z)-4-[(tert-butylamino)methylene]-2-pentenedioate (1.2 g) in MeOH (10 mL) was added 28% sodium methoxide in MeOH (1.9 mL), and the mixture was heated to reflux for 8 hr under a nitrogen atmosphere. The solvent was evaporated in vacuo, and the residue was diluted with EtOAc (20 mL). The resulting mixture was washed successively with 1 M HCl (20 mL), saturated aqueous NaHCO$_3$ (20 mL) and brine, dried over MgSO$_4$ and evaporated in vacuo to give ethyl 1-(tert-butyl)-6-oxo-1,6-dihydro-3-pyridinecarboxylate (657 mg).

Mass ESI (+) 224 (M+H)

$^1$H-NMR (CDCl$_3$) δ 1.35 (3H, t, J=7.15 Hz), 1.70 (9H, s), 4.31 (2H, q, J=7.14 Hz), 6.44 (1H, d, J=9.37 Hz), 7.77 (1H, dd, J=9.45 and 2.44 Hz), 8.44 (1H, d, J=2.38 Hz)

Preparation 12

Ethyl 1-(2,6-dimethylphenyl)-6-oxo-1,6-dihydro-3-pyridinecarboxylate was obtained according to a similar manner to Preparation 11.

Mass ESI (+) 294 (M+Na)

$^1$H-NMR (CDCl$_3$) δ 1.35 (3H, t, J=7.24 Hz), 2.10 (6H, s), 4.32 (2H, q, J=7.10 Hz), 6.70 (1H, d, J=10.04 Hz), 7.17-7.32 (3H, m), 7.95-8.02 (2H, m)

Preparation 13

To a solution of (2,6-difluorophenyl)amine (15.5 g) in THF (140 mL) was added dropwise an 1 M THF solution of lithium 1,1,1,3,3,3-hexamethyldisilazan-2-ide (120 mL) at 0° C. under a nitrogen atmosphere, and the mixture was stirred at the same temperature for 30 min. To the solution was added a solution of dimethyl (2E,4Z)-4-(methoxymethylene)-2-pentenedioate (20 g) in THF (60 mL) at 0° C., and the resulting mixture was stirred at the same temperature for 2 hr. The reaction was quenched with a mixture of EtOAc (200 mL) and 0.5 M HCl (200 mL). The aqueous layer was extracted with EtOAc (200 mL). The organic layers were combined, washed with brine, dried over MgSO$_4$, filtered and evaporated in vacuo. The residue was diluted with MeOH (100 mL), and to the resulting solution was added 28% sodium methoxide in MeOH (38.6 mL). The resulted mixture was heated to reflux for 6 hr under a nitrogen atmosphere. The reaction mixture was concentrated under reduced pressure and the residue was partitioned between EtOAc (200 mL) and 1 M HCl (300 mL). The aqueous layer was separated and extracted with EtOAc (200 mL). The organic layers were combined, washed with saturated aqueous NaHCO$_3$ (300 mL) and brine successively, dried over MgSO$_4$ and evaporated in vacuo. The residue was triturated with IPE, and the precipitates produced were collected by filtration to give methyl 1-(2,6-difluorophenyl)-6-oxo-1,6-dihydro-3-pyridinecarboxylate (5.34 g).

Mass ESI (+) 288 (M+Na)

$^1$H-NMR (CDCl$_3$) δ 3.87 (3H, s), 6.67 (1H, d, J=9.76 Hz), 7.08-7.13 (2H, m), 7.42-7.50 (1H, m), 7.94 (1H, dd, J=9.72 and 2.64 Hz), 8.09 (1H, t, J=1.4 Hz)

Preparation 14

Methyl 1-(4-chloro-2,6-dimethylphenyl)-6-oxo-1,6-dihydro-3-pyridinecarboxylate was obtained according to a similar manner to Preparation 13.

Mass ESI (+) 314 (M+Na)

$^1$H-NMR (CDCl$_3$) δ 2.07 (6H, s), 3.86 (3H, s), 6.69 (1H, dd, J=8.74 and 1.58 Hz), 7.19 (2H, s), 7.95-8.01 (2H, m)

Preparation 15

Methyl 1-(2,3-difluorophenyl)-6-oxo-1,6-dihydro-3-pyridinecarboxylate was obtained according to a similar manner to Preparation 13.

Mass ESI (+) 288 (M+Na)

$^1$H-NMR (CDCl$_3$) δ 3.85 (3H, s), 6.66 (1H, dd, J=9.68 and 0.56 Hz), 7.13-7.17 (1H, m), 7.22-7.27 (1H, m), 7.28-7.36 (1H, m), 7.94 (1H, d, J=9.80 Hz), 8.14 (1H, d, J=1.92 Hz)

Preparation 16

Methyl 6-oxo-1-(1-phenylethyl)-1,6-dihydro-3-pyridinecarboxylate was obtained according to a similar manner to Preparation 13.

Mass ESI (+) 280 (M+Na)

¹H-NMR (CDCl₃) δ 1.76 (3H, d, J=7.18 Hz), 3.77 (3H, s), 6.40 (1H, q, J=7.12 Hz), 6.56 (1H, d, J=9.50 Hz), 7.28-7.43 (5H, m), 7.80 (1H, dd, J=9.52 and 2.50 Hz), 8.04 (1H, d, J=2.46 Hz)

Preparation 17

To a solution of dimethyl (2E,4Z)-4-(methoxymethylene)-2-pentenedioate (1.23 g) in DMF (30 mL) was added cyclohexanamine (670 mg) at 0° C., and the mixture was stirred at the same temperature for 30 min under a nitrogen atmosphere. The reaction mixture was heated to reflux for 5 hr. The mixture was cooled with an ice-water bath and poured into water (100 mL). The resulted mixture was extracted with EtOAc (100 mL×2), and the organic phases were combined, washed with brine two times, dried over MgSO₄, filtered and evaporated in vacuo. The residue was purified by silica gel column chromatography eluting with EtOAc-hexane (1:2-1:1) to give methyl 1-cyclohexyl-6-oxo-1,6-dihydro-3-pyridinecarboxylate (520 mg).

Mass ESI (+) 258 (M+Na)

¹H-NMR (CDCl₃) δ 1.22-1.27 (1H, m), 1.48-1.53 (4H, m), 1.75-1.79 (1H, m), 1.91-1.95 (4H), m), 3.86 (3H, s), 4.84-4.86 (1H, m), 6.53 (1H, d, J=9.36 Hz), 7.80 (1H, dd, J=9.4 and 2.44 Hz), 8.21 (1H, d, J=2.44 Hz)

Preparation 18

Methyl 1-(2-methylphenyl)-6-oxo-1,6-dihydro-3-pyridinecarboxylate was obtained according to a similar manner to Preparation 17.

Mass ESI (+) 266 (M+Na)

¹H-NMR (CDCl₃) δ 2.16 (3H, s), 3.85 (3H, s), 6.65 (1H, d, 9.94 Hz), 7.16-7.22 (1H, m), 7.29-7.40 (3H, m), 7.95 (1H, dd, J=9.62 and 2.54 Hz), 8.11 (1H, d, J=2.60 Hz)

Preparation 19

To a solution of 3-amino-4-chlorobenzoic acid (3.99 g) in THF (35 mL) was added dropwise an 1 M THF solution of lithium 1,1,1,3,3,3-hexamethyldisilazan-2-ide (46.5 mL) while keeping the internal temperature below −5° C. under a nitrogen atmosphere, and the mixture was stirred for 15 min around −10° C. Powder of methyl 1-(2,6-dichlorophenyl)-6-oxo-1,6-dihydro-3-pyridinecarboxylate (3.46 g) was added to the mixture at once, and the resulted mixture was stirred at the same temperature for 3 hr under a nitrogen atmosphere. The reaction mixture was poured into a mixture of ice-water (700 mL) and 1 M HCl (100 mL), and the resulting mixture was extracted with EtOAc (150 mL×3). During the extraction, undissolved materials were produced, which were removed by filtration. The combined organic layers were washed with brine, dried over MgSO₄ and filtered. The filtrate was evaporated in vacuo, and the residue was triturated with MeOH, and the precipitates produced were collected by filtration to give 4-chloro-3-({[1-(2,6-dichlorophenyl)-6-oxo-1,6-dihydro-3-pyridinyl]carbonyl}amino)benzoic acid (1.74 g).

Mass ESI (−) 437 (M−H)

¹H-NMR (DMSO-d₆) δ 6.72 (1H, d, J=9.74 Hz), 7.57-7.89 (6H, m), 8.08-8.17 (2H, m), 8.48 (1H, d, J=2.42 Hz), 10.04 (1H, s), 13.3 (1H, br s)

Preparation 20

3-({[1-(2,6-Dichlorophenyl)-6-oxo-1,6-dihydro-3-pyridinyl]carbonyl}amino)-4-methylbenzoic acid was obtained according to a similar manner to Preparation 19.

Mass ESI (−) 415 (M−H)

¹H-NMR (CD₃OD) δ 2.33 (3H, s), 6.77 (1H, d, J=9.56 Hz), 7.39 (1H, d, J=8.02 Hz), 7.54-7.69 (3H, m), 7.85 (1H, dd, J=7.96 and 1.44 Hz), 7.95 (1H, s), 8.19-8.28 (2H, m)

Preparation 21

4-Chloro-3-({[1-(4-chloro-2,6-dimethylphenyl)-6-oxo-1,6-dihydro-3-pyridinyl]carbonyl}amino)benzoic acid was obtained according to a similar manner to Preparation 19.

Mass ESI (−) 429 (M−H)

¹H-NMR (DMSO-d₆) δ 2.05 (6H, s), 6.67 (1H, d, J=9.76 Hz), 7.40 (2H, s), 7.67 (1H, d, J=8.40 Hz), 7.80 (1H, dd, J=8.36 and 2.08 Hz), 8.05-8.31 (2H, m), 8.32 (1H, s), 9.98 (1H, s), 13.55 (1H, br s)

Preparation 22

4-Chloro-3-({[1-(2,6-dimethyl-4-fluorophenyl)-6-oxo-1,6-dihydro-3-pyridinyl]carbonyl}amino)benzoic acid was obtained according to a similar manner to Preparation 19.

Mass ESI (−) 413 (M−H)

¹H-NMR (DMSO-d₆) δ 2.49 (6H, s), 6.67 (1H, d, J=9.72 Hz), 7.17 (2H, d, J=9.32 Hz), 7.67 (1H, d, J=8.32 Hz), 7.80 (1H, dd, J=8.32 and 2.00 Hz), 8.05-8.10 (2H, m), 8.32 (1H, d, J=2.40 Hz), 9.99 (1H, s), 13.23 (1H, br s)

Preparation 23

4-Chloro-3-({[(1-cyclohexyl)-6-oxo-1,6-dihydro-3-pyridinyl]carbonyl}amino)benzoic acid was obtained according to a similar manner to Preparation 19.

Mass ESI (−) 373 (M−H)

¹H-NMR (DMSO-d₆) δ 1.21-1.26 (1H, m), 1.39-1.45 (2H, m), 1.65-1.73 (3H, m), 1.74-1.88 (4H, m), 4.66-4.73 (1H, m), 6.49 (1H, d, J=9.52 Hz), 7.69 (1H, d, J=8.36 Hz), 7.82 (1H, dd, J=8.36 and 2.00 Hz), 7.91 (1H, dd, J=9.52 and 2.52 Hz), 8.07 (1H, d, J=2.00 Hz), 8.46 (1H, d, J=2.48 Hz), 10.04 (1H, s), 13.28 (1H, s, br s)

Preparation 24

To a solution of methyl 1-(2,6-difluorophenyl)-6-oxo-1,6-dihydro-3-pyridinecarboxylate (5.41 g) in a mixture of EtOH (108 mL) and THF (54 mL) was added 1 M aqueous NaOH (82 mL) at 0° C., and the mixture was stirred at the same temperature for 2 hr. The mixture was concentrated under reduced pressure and the residue was treated with 1 M HCl (160 mL). The precipitates produced were collected by filtration and dried under reduced pressure at 60° C. to give 1-(2,6-difluorophenyl)-6-oxo-1,6-dihydro-3-pyridinecarboxylic acid (4.73 g).

Mass ESI (−) 250 (M−H)

¹H-NMR (DMSO-d₆) δ 6.62 (1H, d, J=9.64 Hz), 7.30-7.39 (2H, m), 7.55-7.67 (1H, m), 7.92-7.95 (1H, dd, J=9.64 and 2.56 Hz), 13.12 (1H, br s)

Preparation 25

1-(2-Chloro-6-fluorophenyl)-6-oxo-1,6-dihydro-3-pyridinecarboxylic acid was obtained according to a similar manner to Preparation 24.

Mass ESI (−) 266 (M−H)

¹H-NMR (DMSO-d₆) δ 6.62 (1H, d, J=9.68 Hz), 7.43-7.51 (1H, m), 7.56-7.64 (2H, m), 7.94 (1H, dd, J=9.80 and 2.56 Hz), 8.38 (1H, d, J=2.44 Hz), 13.06 (1H, s)

Preparation 26

1-(2,3-Difluorophenyl)-6-oxo-1,6-dihydro-3-pyridinecarboxylic acid was obtained according to a similar manner to Preparation 24.

Mass ESI (−) 250 (M−H)

¹H-NMR (DMSO-d₆) δ 6.58 (1H, d, J=9.68 Hz), 7.27-7.47 (2H, m), 7.59-7.66 (1H, m), 7.78-7.93 (1H, m), 8.34 (1H, d, J=2.4 Hz), 13.05 (1H, br s)

Preparation 27

1-(2,6-Dichlorophenyl)-6-oxo-1,6-dihydro-3-pyridinecarboxylic acid was obtained according to a similar manner to Preparation 24.

Mass ESI (−) 282 (M−H)

¹H-NMR (CDCl₃₊CD₃OD) δ 6.70 (1H, dd, J=8.80 and 1.4 Hz), 7.35-7.56 (3H, m), 8.02-8.07 (2H, m)

Preparation 28

1-(2-Methylphenyl)-6-oxo-1,6-dihydro-3-pyridinecarboxylic acid was obtained according to a similar manner to Preparation 24.

Mass ESI (−) 228 (M−H)

$^1$H-NMR (CD$_3$OD) δ 2.12 (3H, s), 6.65 (1H, d, J=9.64 Hz), 7.24-7.49 (4H, m), 8.09 (1H, dd, J=9.52 and 2.50 Hz), 8.21 (1H, d, J=2.36 Hz)

Preparation 29

1-tert-Butyl-6-oxo-1,6-dihydro-3-pyridinecarboxylic acid was obtained according to a similar manner to Preparation 24.

Mass ESI (−) 194 (M−H)

$^1$H-NMR (CDCl$_3$-CD$_3$OD) δ 1.71 (9H, s), 6.46 (1H, d, J=9.32 Hz), 7.82 (1H, dd, J=9.44 and 2.42 Hz), 8.48 (1H, d, J=2.34 Hz)

Preparation 30

1-(2,6-Dimethylphenyl)-6-oxo-1,6-dihydro-3-pyridinecarboxylic acid was obtained according to a similar manner to Preparation 24.

Mass ESI (−) 242 (M−H)

$^1$H-NMR (CD$_3$OD) δ 2.06 (6H, s), 6.70 (1H, d, J=10.20 Hz), 7.21-7.35 (3H, m), 8.08-8.15 (2H, m)

Preparation 31

1-(2-Chloro-6-fluorophenyl)-6-oxo-1,6-dihydro-3-pyridinecarboxylic acid was obtained according to a similar manner to Preparation 24.

Mass ESI (−) 266 (M−H)

$^1$H-NMR (DMSO-d$_6$) δ 6.62 (1H, d, J=9.68 Hz), 7.43-7.51 (1H, m), 7.56-7.64 (2H, m), 7.94 (1H, dd, J=9.80 and 2.56 Hz), 8.38 (1H, d, J=2.44 Hz), 13.06 (1H, s)

Preparation 32

6-Oxo-1-(1-phenylethyl)-1,6-dihydro-3-pyridinecarboxylic acid was obtained according to a similar manner to Preparation 24.

Mass ESI (−) 242 (M−H)

$^1$H-NMR (CD$_3$OD) δ 1.78 (3H, d, J=7.14 Hz), 6.29 (1H, q, J=7.10 Hz), 6.57 (1H, d, J=9.46 Hz), 7.28-7.45 (5H, m), 7.92 (1H, dd, J=9.36 and 2.40 Hz), 8.19 (1H, d, J=2.40 Hz)

Preparation 33

To a suspension of 1-(2,6-difluorophenyl)-6-oxo-1,6-dihydro-3-pyridinecarboxylic acid (795 mg) in CH$_2$Cl$_2$ (8 mL) were added DMF (0.025 mL) and ethanedioyl dichloride (603 mg) at 0° C. under a nitrogen atmosphere, and the mixture was stirred at room temperature for 2 hr. The volatile materials were removed by evaporation in vacuo to give 1-(2,6-difluorophenyl)-6-oxo-1,6-dihydro-3-pyridinecarbonyl chloride (810 mg).

$^1$H-NMR (CDCl$_3$) δ 6.68-6.72 (1H, m), 7.09-7.17 (2H, m), 7.44-7.55 (1H, m), 7.92-7.97 (1H, m), 8.31 (1H, dd, J=2.72 and 0.56 Hz)

Preparation 34

1-(2-Chloro-6-fluorophenyl)-6-oxo-1,6-dihydro-3-pyridinecarbonyl chloride was obtained according to a similar manner to Preparation 33.

$^1$H-NMR (CDCl$_3$) δ 6.71 (1H, d, J=9.84 Hz), 7.23-7.27 (1H, m), 7.41-7.52 (2H, m), 7.95 (1H, dd, J=9.88 and 2.72 Hz), 8.12 (1H, s)

Preparation 35

To a solution of 3-amino-4-chlorobenzoic acid (509 mg) in THF (8 mL) was added dropwise an 1 M THF solution of lithium 1,1,1,3,3,3-hexamethyldisilazan-2-ide (6 mL) while keeping the internal temperature below −5° C. under a nitrogen atmosphere, and the mixture was stirred around −5° C. for 30 min. To the solution was added dropwise a solution of 1-(2,6-difluorophenyl)-6-oxo-1,6-dihydro-3-pyridinecarbonyl chloride (800 mg) in THF (8 ml), and the resulting mixture was stirred around −5° C. for 1 hr. The reaction mixture was partitioned between EtOAc (16 mL) and 1 M HCl (16 mL). The aqueous layer was extracted with EtOAc (8 mL). The organic layers were combined, washed with brine two times, dried over MgSO$_4$, filtered and evaporated in vacuo. The residue was triturated with CH$_2$Cl$_2$, and the precipitates produced were collected by filtration. The isolated product was triturated with MeOH and collected by filtration to give 4-chloro-3-({[1-(2,6-difluorophenyl)-6-oxo-1,6-dihydro-3-pyridinyl]carbonyl}amino)benzoic acid (288 mg).

Mass ESI (−) 403 (M−H)

$^1$H-NMR (DMSO-d$_6$) δ 6.70 (1H, d, J=9.76 Hz), 7.34-7.44 (2H, m), 7.64-7.71 (2H, m), 7.82 (1H, dd, J=6.88 and 4.80 Hz), 8.08 (1H, s), 8.10 (1H, dd, J=7.32 and 2.64 Hz), 10.04 (1H, s), 13.27 (1H, br s)

Preparation 36

4-Bromo-3-({[1-(2,6-difluorophenyl)-6-oxo-1,6-dihydro-3-pyridinyl]carbonyl}amino)benzoic acid was obtained according to a similar manner to Preparation 35.

Mass ESI (−) 403 (M−H)

$^1$H-NMR (DMSO-d$_6$) δ 6.70 (1H, d, J=9.76 Hz), 7.34-7.44 (2H, m), 7.64-7.71 (2H, m), 7.82 (1H, dd, J=6.88 and 4.80 Hz), 8.08 (1H, s), 8.10 (1H, dd, J=7.32 and 2.64 Hz), 10.04 (1H, s), 13.27 (1H, br s)

Preparation 37

4-Chloro-3-({[1-(2-chloro-6-fluorophenyl)-6-oxo-1,6-dihydro-3-pyridinyl]carbonyl}amino)benzoic acid was obtained according to a similar manner to Preparation 35.

Mass ESI (−) 419 (M−H)

$^1$H-NMR (DMSO-d$_6$) δ 6.71 (1H, d, J=9.84 Hz), 7.53-7.69 (4H, m), 7.81 (1H, dd, J=8.32 and 2.04 Hz), 8.09-8.13 (2H, m), 8.53 (1H, d, J=2.44 Hz), 10.04 (1H, s), 13.25 (1H, s)

Preparation 38

To a suspension of 1-(2,3-difluorophenyl)-6-oxo-1,6-dihydro-3-pyridinecarboxylic acid (1.24 g) and DMF (0.124 mL) in CH$_2$Cl$_2$ (124 mL) was added ethanedioyl dichloride (940 mg) at 0° C. under a nitrogen atmosphere, and the mixture was stirred at ambient temperature for 1 hr. Additional DMF (0.124 mL) was added, and the mixture was stirred for additional 30 min. The volatile materials were removed by evaporation and the residue was suspended in THF (12.4 mL) and cooled to −78° C. To a solution of 3-amino-4-chlorobenzoic acid (847 mg) in THF (18 mL) was added an 1 M THF solution of lithium 1,1,1,3,3,3-hexamethyldisilazan-2-ide (9.9 mL) at 0° C. under a nitrogen atmosphere, and the mixture was stirred at room temperature for 30 min. The solution was cooled to −78° C., and to the solution was added the suspension of 1-(2,3-difluorophenyl)-6-oxo-1,6-dihydro-3-pyridinecarbonyl chloride in THF (12.4 mL) prepared as described above. The resulted mixture was stirred at −78° C. for 2 hr under a nitrogen atmosphere, and then poured into a mixture of EtOAc (30 mL) and 1 M HCl (20 mL). The aqueous layer was extracted with EtOAc (30 mL) and the organic layers were combined, washed with brine, dried over MgSO$_4$, filtered and evaporated in vacuo. The residue was triturated with MeOH, and the precipitates produced were collected by filtration to give 4-chloro-3-({[1-(2,3-difluorophenyl)-6-oxo-1,6-dihydro-3-pyridinyl]carbonyl}amino)benzoic acid (780 mg).

Mass ESI (−) 403 (M−H)

$^1$H-NMR (DMSO-d$_6$) δ 6.66 (1H, d, J=9.64 Hz), 7.41-7.47 (1H, m), 7.50-7.54 (1H, m), 7.63-7.70 (2H, m), 7.81 (1H, dd, J=8.36 and 2.04 Hz), 7.91 (1H, d, J=2.56 Hz), 7.93 (1H, d, J=2.52 Hz), 8.53 (1H, s), 10.05 (1H, s), 13.27 (1H, br s)

Preparation 39

To a solution of (4-methyl-3-nitrophenyl)amine (304 mg) in DMF (3 mL) were added cyclopropanecarboxylic acid (258 mg), HATU (1.14 g) and iPr$_2$NEt (1.55 g) successively, and the mixture was stirred at room temperature for 16 hr under a nitrogen atmosphere. The reaction mixture was diluted with EtOAc (15 mL) and the resulted mixture was washed with 1 M HCl (15 mL×2), saturated aqueous NaHCO$_3$ (15 mL×2) and brine, dried over MgSO$_4$, filtered and evaporated in vacuo. The residue was purified by silica gel column chromatography eluting with EtOAc-hexane (1:2) to give N-(4-methyl-3-nitrophenyl)cyclopropanecarboxamide (413 mg).

Mass ESI (+) 243 (M+Na)
$^1$H-NMR (CD$_3$OD) δ 0.82-0.88 (2H, m), 0.90-1.00 (2H, m), 2.49 (3H, s), 7.34 (1H, d, J=8.37 Hz), 7.66 (1H, dd, J=8.38 and 2.29% Hz), 8.32 (1H, d, J=2.18 Hz)

Preparation 40

N-(4-Methyl-3-nitrophenyl)cyclopropanecarboxamide (409 mg) was hydrogenated over 10% Pd/C (50% wet, 80 mg) at atmospheric pressure of hydrogen in MeOH (20 mL) for 5 hr. The catalyst was removed by filtration through Celite® pad and the filtrate was evaporated in vacuo to give N-(3-amino-4-methylphenyl)cyclopropanecarboxamide (335 mg).

Mass ESI (+) 213 (M+Na)
$^1$H-NMR (CD$_3$OD) δ 0.75-0.84 (2H, m), 0.87-0.95 (2H, m), 1.65-1.78 (1H, m), 2.09 (3H, s), 6.73 (1H, dd, J=8.04 and 2.04 Hz), 6.89 (1H, d, J=8.06 Hz), 7.00 (1H, d, J=1.98 Hz)

Preparation 41

To a suspension of 3-tert-butyl-1-(4-methylphenyl)-1H-pyrazol-5-amine hydrochloride (2.5 g) in EtOAc (18 ml) was added 2.94 M aqueous NaOH (8 mL) at 0° C. under a nitrogen atmosphere, and the mixture was stirred at the same temperature for 15 min. To the reaction mixture was added 2,2,2-trichloroethyl chlorocarbonate (2.79 g), and the resulting mixture was stirred at room temperature for 6 hr. The organic layer was separated and successively washed with brine (10 mL×2), dried over MgSO$_4$, filtered and evaporated in vacuo. The residue was triturated with IPE, and the precipitates produced were collected by filtration to give 2,2,2-trichloroethyl[3-tert-butyl-1-(4-methylphenyl)-1H-pyrazol-5-yl]carbamate (1.96 g).

Mass ESI (+) 406 (M+H)
$^1$H-NMR (CDCl$_3$) δ 1.34 (9H, s), 2.40 (3H, s), 4.81 (2H, s), 6.41 (1H, s), 6.80 (1H, br s), 7.31-7.37 (4H, m).

Preparation 42

To a mixture of 2,2,2-trichloroethyl[3-tert-butyl-1-(4-methylphenyl)-1H-pyrazol-5-yl]carbamate (101 mg) and (4-methyl-3-nitrophenyl)amine (38 mg) in DMSO (1 mL) was added iPr$_2$NEt (44 under a nitrogen atmosphere and the mixture was stirred at 60° C. for 4 hr. The reaction mixture was diluted with EtOAc (2 mL) and successively washed with 1M HCl (2 mL×2), saturated aqueous NaHCO$_3$ (2 mL) and brine (2 mL), dried over MgSO$_4$ and filtered. The filtrate was evaporated in vacuo, and the residue was purified by silica gel column chromatography eluting with 2% MeOH in CH$_2$Cl$_2$ to give 1-[3-tert-butyl-1-(4-methylphenyl)-1H-pyrazol-5-yl]-3-(4-methyl-3-nitrophenyl)urea (96 mg).

Mass ESI (+) 408 (M+Na)
$^1$H-NMR (CDCl$_3$) δ 1.30 (9H, s), 2.31 (3H, s), 2.52 (3H, s), 6.40 (1H, s), 6.75 (1H, s), 7.12-7.27 (4H, m), 7.52 (1H, dd, J=8.32 and 2.26 Hz), 7.70 (1H, s), 7.90 (1H, d, J=2.20 Hz).

Preparation 43

1-[3-tert-Butyl-1-(4-methylphenyl)-1H-pyrazol-5-yl]-3-(4-methyl-3-nitrophenyl)urea (93 mg) was hydrogenated over 10% Pd/C (50% wet, 10 mg) at atmospheric pressure of hydrogen in MeOH (2 mL) for 4 hr. The catalyst was removed by filtration through Celite® pad and the filtrate was evaporated in vacuo. The residue was triturated with IPE and the precipitates produced were collected by filtration to give 1-(3-amino-4-methylphenyl)-3-[3-tert-butyl-1-(4-methylphenyl)-1H-pyrazol-5-yl]urea (74 mg).

Mass ESI (+) 378 (M+H)
$^1$H-NMR (CDCl$_3$) δ 1.37 (9H, s), 2.32 (3H, s), 2.43 (3H, s), 7.11 (1H, dd, J=8.34 and 2.18 Hz), 7.24-7.32 (2H, m), 7.38 (4H, s), 7.81 (1H, d, J=2.32 Hz)

Preparation 44

To a solution (4-methyl-3-nitrophenyl)amine (152 mg) in CH$_2$Cl$_2$ (15 mL) were added iPr$_2$NEt (1.29 g) and trichloroacetic anhydride (370 mg) successively at 0° C. under a nitrogen atmosphere, and the mixture was stirred at 0° C. for 3 hr. To the solution was added phenylamine (930 mg), and the resulted mixture was stirred at room temperature for 16 h. The volatile materials were evaporated in vacuo. The residue was diluted with EtOAc (10 mL) and the resulted mixture was successively washed with 1M HCl (5 mL×2), saturated aqueous NaHCO$_3$ (5 mL×2) and brine, dried over MgSO$_4$ and filtered. The filtrate was evaporated in vacuo, and the residue was triturated with IPE. The precipitates produced were collected by filtration to give 1-(4-methyl-3-nitrophenyl)-3-phenylurea (270 mg).

Mass ESI (+) 294 (M+Na)
$^1$H-NMR (DMSO-d$_6$) δ 2.45 (3H, s), 6.95-7.02 (1H, m), 7.25-7.57 (6H, m), 8.29 (1H, d, J=2.24 Hz), 8.81 (1H, s), 9.08 (1H, s)

Preparation 45

1-Cyclopropyl-3-(4-methyl-3-nitrophenyl)urea was obtained according to a similar manner to Preparation 44.

Mass ESI (+) 258 (M+Na)
$^1$H-NMR (CDCl$_3$) δ 0.46-0.54 (2H, m), 0.70-0.79 (2H, m), 2.47 (3H, s), 2.52-2.63 (1H, m), 7.28 (1H, d, J=8.40 Hz), 7.50 (1H, dd, J=8.34 and 2.30 Hz), 8.16 (1H, d, J=2.32 Hz)

Preparation 46

1-(3-Amino-4-methylphenyl)-3-phenylurea was obtained according to a similar manner to Preparation 43.

Mass ESI (+) 264 (M+Na)
$^1$H-NMR (DMSO-d$_6$) δ 1.97 (3H, s), 4.79 (2H, s), 6.53 (1H, d, J=7.85 Hz), 6.76-6.79 (2H, m), 6.94 (1H, d, J=7.33 Hz), 7.25 (2H, t, J=7.74 Hz), 7.42 (2H, d, J=7.75 Hz), 8.32 (1H, s), 8.55 (1H, s)

Preparation 47

1-(3-Amino-4-methylphenyl)-3-cyclopropylurea was obtained according to a similar manner to Preparation 43.

Mass ESI (+) 228 (M+Na)
$^1$H-NMR (DMSO-d$_6$) δ 0.31-0.39 (2H, m), 1.95 (3H, s), 4.69 (2H, s), 6.21 (1H, d, J=2.54 Hz), 6.49 (1H, dd, J=7.96 and 2.10 Hz), 6.67-6.74 (2H, m), 7.87 (1H, s)

EXAMPLE 1

To a solution of 4-chloro-3-({[1-(2,6-dichlorophenyl)-6-oxo-1,6-dihydro-3-pyridinyl]carbonyl}amino)benzoic acid (1.74 g) in DMF (17 mL) were added HATU (3.03 g), cyclopropanamine (680 mg) and iPr$_2$NEt (3.08 g) successively at 0° C., and the mixture was stirred at room temperature for 16 hr under a nitrogen atmosphere. The mixture was partitioned between EtOAc (50 mL) and 1 M HCl (50 mL), and the precipitates produced were removed by filtration. The organic layer of the filtrate was separated and washed with 1 M HCl (50 mL), saturated aqueous NaHCO$_3$ (50 mL×2) and brine successively, dried over MgSO$_4$ and filtered. The filtrate was evaporated in vacuo, and the residue was triturated with a mixture of IPE and MeOH. The precipitates were collected by filtration, triturated with EtOH and collected by filtration to give N-{2-chloro-5-[(cyclopropylamino)carbonyl]phenyl}-1-(2,6-dichlorophenyl)-6-oxo-1,6-dihydro-3-pyridinecarboxamide (890 mg).

Mass ESI (+) 498 (M+Na)

¹H-NMR (DMSO-d₆) δ 0.52-0.59 (2H, m), 0.61-0.74 (2H, m), 2.78-2.91 (1H, m), 6.72 (1H, d, J=9.74 Hz), 7.58-7.79 (4H, m), 7.97 (1H, d, J=1.96 Hz), 8.14 (1H, dd, J=9.66 and 2.56 Hz), 8.47 (1H, d, J=2.46 Hz), 8.52 (1H, d, J=4.14 Hz), 10.03 (1H, s)

EXAMPLE 2

N-{2-Chloro-5-[(methoxyamino)carbonyl]phenyl}-1-(2,6-dichlorophenyl)-6-oxo-1,6-dihydro-3-pyridinecarboxamide was obtained according to a similar manner to Example 1.
Mass ESI (+) 490 (M+Na)
¹H-NMR (DMSO-d₆) δ 3.70 (3H, s), 6.71 (1H, d, J=9.80 Hz), 7.60-7.68 (3H, m), 7.76-7.78 (2H, m), 7.92 (1H, d, J=1.52 Hz), 8.13 (1H, dd, J=9.72 and 2.64 Hz), 8.48 (1H, d, J=2.40 Hz), 10.04 (1H, s), 11.86 (1H, s)

EXAMPLE 3

N-{2-Chloro-5-[(isoxazol-3-ylamino)carbonyl]phenyl}-1-(2,6-dichlorophenyl)-6-oxo-1,6-dihydro-3-pyridinecarboxamide was obtained according to a similar manner to Example 1.
Mass ESI (+) 526 (M+Na)
¹H-NMR (DMSO-d₆) δ 6.72 (1H, d, J=9.80 Hz), 7.04 (1H, d, J=1.64 Hz), 7.60-7.64 (2H, m), 7.71-7.78 (3H, m), 7.94 (1H, dd, J=8.44 and 2.16 Hz), 8.15 (1H, dd, J=9.68 and 2.56 Hz), 8.23 (1H, d, J=2.20 Hz), 8.50 (1H, d, J=2.40 Hz), 8.86 (1H, d, J=1.68 Hz), 10.07 (1H, s)

EXAMPLE 4

N-{2-Chloro-5-[(pyridin-3-ylamino)carbonyl]phenyl}-1-(2,6-dichlorophenyl)-6-oxo-1,6-dihydro-3-pyridinecarboxamide was obtained according to a similar manner to Example 1.
Mass ESI (+) 537 (M+Na)
¹H-NMR (DMSO-d₆) δ 6.72 (1H, d, J=9.72 Hz), 7.41 (1H, dd, J=8.32 and 4.88 Hz), 7.62 (1H, dd, J=8.68 and 7.44 Hz), 7.73-7.78 (3H, m), 7.93 (1H, dd, J=8.44 and 2.08 Hz), 8.16-8.20 (3H, m), 8.33 (1H, dd, J=4.76 and 1.48 Hz), 8.53 (1H, d, J=2.44 Hz), 8.93 (1H, d, J=2.56 Hz), 10.18 (1H, s), 10.58 (1H, s)

EXAMPLE 5

N-{2-Chloro-5-[(1-methyl-1H-pyrazol-3-ylamino)carbonyl]phenyl}-1-(2,6-dichlorophenyl)-6-oxo-1,6-dihydro-3-pyridinecarboxamide was obtained according to a similar manner to Example 1.
Mass ESI (+) 540 (M+Na)
¹H-NMR (DMSO-d₆) δ 3.78 (3H, s), 6.58 (1H, d, J=2.0 Hz), 6.72 (1H, d, J=9.6 Hz), 7.60-7.67 (3H, m), 7.77 (2H, d, J=8.0 Hz), 7.91 (1H, dd, J=8.0 and 1.6 Hz), 8.17 (1H, dd, J=10.0 and 2.8 Hz), 8.20 (1H, d, J=2.0 Hz), 8.49 (1H, d, J=2.8 Hz), 10.04 (1H, s), 10.93 (1H, s)

EXAMPLE 6

N-{2-Chloro-5-[(1-methyl-1H-pyrazol-5-ylamino)carbonyl]phenyl}-1-(2,6-dichlorophenyl)-6-oxo-1,6-dihydro-3-pyridinecarboxamide was obtained according to a similar manner to Example 1.
Mass ESI (+) 538 (M+Na)
¹H-NMR (DMSO-d₆) δ 3.68 (3H, s), 6.23 (1H, d, J=2.0 Hz), 6.72 (1H, d, J=9.6 Hz), 7.39 (1H, d, J=2.0 Hz), 7.62 (1H, dd, J=8.8 and 7.6 Hz), 7.73-7.78 (3H, m), 7.88 (1H, d, J=2.0 Hz), 8.13-8.16 (2H, m), 8.50 (1H, d, J=2.4 Hz), 10.09 (1H, s), 10.40 (1H, s)

EXAMPLE 7

N-{2-Chloro-5-[(1-phenyl-1H-pyrazol-5-ylamino)carbonyl]phenyl}-1-(2,6-dichlorophenyl)-6-oxo-1,6-dihydro-3-pyridinecarboxamide was obtained according to a similar manner to Example 1.
Mass ESI (+) 602 (M+Na)
¹H-NMR (DMSO-d₆) δ 6.48 (1H, s), 6.71 (1H, d, J=9.64 Hz), 7.32-7.79 (11H, m), 8.04 (1H, s), 8.13 (1H, dd, J=9.76 and 2.64 Hz), 8.48 (1H, d, J=2.36 Hz), 10.06 (1H, s), 10.49 (1H, s)

EXAMPLE 8

N-{2-Chloro-5-[(cyclopropylamino)carbonyl]phenyl}-1-(2,6-dichloro-4-methylphenyl)-6-oxo-1,6-dihydro-3-pyridinecarboxamide was obtained according to a similar manner to Example 1.
Mass ESI (+) 492 (M+Na)
¹H-NMR (DMSO-d₆) δ 0.54-0.58 (2H, m), 0.66-0.71 (2H, m), 2.04 (6H, s), 2.82-2.86 (1H, m), 6.67 (1H, d, J=9.64 Hz), 7.41 (2H, s), 7.62 (1H, d, J=8.39 Hz), 7.72 (1H, dd, J=8.39 and 2.08 Hz), 7.97 (1H, d, J=2.10 Hz), 8.08 (1H, dd, J=9.63 and 2.65 Hz), 8.32 (1H, d, J=2.60 Hz), 8.53 (1H, s), 9.99 (1H, s)

EXAMPLE 9

N-{2-Chloro-5-[(cyclopropylamino)carbonyl]phenyl}-1-cyclohexyl-6-oxo-1,6-dihydro-3-pyridinecarboxamide was obtained according to a similar manner to Example 1.
Mass ESI (+) 436 (M+Na)
¹H-NMR (DMSO-d₆) δ 0.56-0.59 (2H, m), 0.67-0.70 (2H, m), 1.20-1.28 (1H, m), 1.36-1.47 (2H, m), 1.63-1.74 (3H, m), 1.73-1.88 (4H, m), 2.83-2.89 (1H, m), 4.67-4.74 (1H, m), 6.50 (1H, d, J=9.52 Hz), 7.63 (1H, d, J=8.40 Hz), 7.75 (1H, dd, J=8.40 and 2.20 Hz), 7.91 (1H, dd, J=9.40 and 2.48 Hz), 7.96 (1H, d, J=1.88 Hz), 8.46 (1H, d, J=2.48 Hz), 8.54 (1H, d, J=4.16 Hz), 10.04 (1H, s)

EXAMPLE 10

N-{2-Chloro-5-[(cyclopropylamino)carbonyl]phenyl}-1-(2,6-dimethyl-4-fluorophenyl)-6-oxo-1,6-dihydro-3-pyridinecarboxamide was obtained according to a similar manner to Example 1.
Mass ESI (+) 476 (M+Na)
¹H-NMR (DMSO-d₆) δ 0.54-0.58 (2H, m), 0.66-0.71 (2H, m), 2.05 (6H, s), 2.83-2.85 (1H, m), 6.67 (1H, d, J=9.60 Hz), 7.17 (2H, d, J=9.31 Hz), 7.62 (1H, d, J=8.36 Hz), 7.72 (1H, dd, J=8.35 and 2.01 Hz), 7.97 (1H, d, J=2.08 Hz), 8.08 (1H, dd, J=9.57 and 2.54 Hz), 8.32 (1H, d, J=2.56 Hz), 4.14 Hz), 9.99 (1H, s)

EXAMPLE 11

N-{2-Chloro-5-[(cyclopropylamino)carbonyl]phenyl}-1-(2,6-difluorophenyl)-6-oxo-1,6-dihydro-3-pyridinecarboxamide was obtained according to a similar manner to Example 1.
Mass ESI (+) 466 (M+Na)
¹H-NMR (DMSO-d₆) δ 0.54-0.58 (2H, m), 0.67-0.71 (2H, m), 2.81-3.31 (1H, m), 6.70 (1H, d, J=9.76 Hz), 7.42 (2H, t, J=8.28 Hz), 7.62-7.74 (3H, m), 7.97 (1H, d, J=2.12 Hz), 8.10 (1H, dd, J=9.72 and 2.76 Hz), 8.53 (1H, d, J=4.16 Hz), 8.58 (1H, d, J=2.48 Hz), 10.03 (1H, s)

EXAMPLE 12

N-{2-Chloro-5-[(1-methyl-1H-pyrazol-5-ylamino)carbonyl]phenyl}-1-(2,6-difluorophenyl)-6-oxo-1,6-dihydro-3-pyridinecarboxamide was obtained according to a similar manner to Example 1.

Mass ESI (+) 506 (M+Na)

$^1$H-NMR (DMSO-$d_6$) 3.69 (3H, s), 6.23 (1H, d, J=1.92 Hz), 6.71 (1H, d, J=9.64 Hz), 7.39-7.44 (3H, m), 7.66-7.70 (2H, m), 7.74 (1H, d, J=8.40 Hz), 7.90 (1H, dd, J=8.40 and 2.04 Hz), 8.10-8.14 (2H, m), 8.60 (1H, d, J=2.52 Hz), 10.1 (1H, br s), 10.42 (1H, br s)

EXAMPLE 13

N-{2-Chloro-5-[(cyclopropylmethoxyamino)carbonyl]phenyl}-1-(2,6-difluorophenyl)-6-oxo-1,6-dihydro-3-pyridinecarboxamide was obtained according to a similar manner to Example 1.

Mass ESI (+) 496 (M+Na)

$^1$H-NMR (DMSO-$d_6$) 0.24-0.27 (2H, m), 0.51-0.55 (2H, m), 1.08-1.12 (1H, m), 3.65-3.71 (2H, m), 6.71 (1H, d, J=9.84 Hz), 7.42 (2H, t, J=8.20 Hz), 7.64-7.71 (3H, m), 7.92 (1H, d, J=1.60 Hz), 8.10 (1H, dd, J=9.72 and 1.60 Hz), 8.58 (1H, d, J=2.52 Hz), 10.04 (1H, s), 11.75 (1H, s, J=11.76 Hz)

EXAMPLE 14

N-{2-Chloro-5-[(1-methyl-1H-pyrazol-3-ylamino)carbonyl]phenyl}-1-(2,6-difluorophenyl)-6-oxo-1,6-dihydro-3-pyridinecarboxamide was obtained according to a similar manner to Example 1.

Mass ESI (+) 506 (M+Na)

$^1$H-NMR (DMSO-$d_6$) δ 3.78 (3H, s), 6.58 (1H, d, J=2.20 Hz), 6.71 (1H, d, J=9.72 Hz), 7.40-7.45 (2H, m), 7.61-7.70 (3H, m), 7.91 (1H, dd, J=8.44 and 2.16 Hz), 8.12 (1H, dd, J=9.72 and 2.60 Hz), 8.19 (1H, d, J=2.16 Hz), 8.60 (1H, d, J=2.52 Hz), 10.05 (1H, s), 10.94 (1H, s)

EXAMPLE 15

N-{2-Bromo-5-[(cyclopropylamino)carbonyl]phenyl}-1-(2,6-difluorophenyl)-6-oxo-1,6-dihydro-3-pyridinecarboxamide was obtained according to a similar manner to Example 1.

Mass ESI (+) 512 (M+Na)

$^1$H-NMR (DMSO-$d_6$) δ 0.55-0.58 (2H, m), 0.67-0.70 (2H, m), 2.83-2.86 (1H, m), 6.71 (1H, d, J=9.76 Hz), 7.40-7.44 (2H, m), 7.64-7.68 (2H, m), 7.79 (1H, d, J=8.40 Hz), 7.92 (1H, d, J=2.08 Hz), 8.11 (1H, dd, J=9.72 and 2.60 Hz), 8.54 (1H, d, J=4.20 Hz), 8.57 (1H, d, J=2.92 Hz), 10.02 (1H, s)

EXAMPLE 16

N-{2-Chloro-5-[(cyclopropylamino)carbonyl]phenyl}-1-(2-chloro-6-fluorophenyl)-6-oxo-1,6-dihydro-3-pyridinecarboxamide was obtained according to a similar manner to Example 1.

Mass ESI (+) 482 (M+Na)

$^1$H-NMR (DMSO-$d_6$) δ 0.54-0.58 (2H, m), 0.67-0.71 (2H, m), 2.82-2.87 (1H, m), 6.71 (1H, d, J=9.76 Hz), 7.53-7.58 (1H, m), 7.62-7.67 (3H, m), 7.73 (1H, dd, J=8.40 and 2.04 Hz), 7.97 (1H, d, J=2.04 Hz), 8.12 (1H, dd, J=9.72 and 2.60 Hz), 8.52 (2H, d, J=2.76 Hz), 10.02 (1H, s)

EXAMPLE 17

N-{2-Chloro-5-[(cyclopropylamino)carbonyl]phenyl}-1-(2,3-difluorophenyl)-6-oxo-1,6-dihydro-3-pyridinecarboxamide was obtained according to a similar manner to Example 1.

Mass ESI (+) 466 (M+Na)

$^1$H-NMR (DMSO-$d_6$) δ 0.54-0.58 (2H, m), 0.67-0.71 (2H, m), 2.82-2.87 (1H, m), 6.66 (1H, d, J=9.52 Hz), 7.43-7.47 (2H, m), 7.50-7.74 (3H, m), 7.96 (1H, d, J=2.08 Hz), 8.08 (1H, dd, J=9.68 and 2.60 Hz), 8.52 (1H, s), 8.54 (1H, d, J=5.20 Hz), 10.03 (1H, s)

EXAMPLE 18

To a solution of 1-(2,6-dichlorophenyl)-6-oxo-1,6-dihydro-3-pyridinecarboxylic acid (56 mg) in DMF (0.76 mL) were added 3-amino-N-cyclopropyl-4-methylbenzamide (45 mg), WSC—HCl (57 mg), HOBt (35 mg) and Et$_3$N (27 mg), and the mixture was stirred under a nitrogen atmosphere at room temperature for 16 hr. The reaction mixture was diluted with EtOAc (2 mL), washed with water (4 mL×2) and brine successively, dried over MgSO$_4$, filtered and evaporated in vacuo. The residue was purified by preparative thin layer chromatography eluting with 10% MeOH in CH$_2$Cl$_2$ to give N-{5-[(cyclopropylamino)carbonyl]-2-methylphenyl}-1-(2,6-dichlorophenyl)-6-oxo-1,6-dihydro-3-pyridinecarboxamide (60 mg).

Mass ESI (+) 480 (M+Na)

$^1$H-NMR (CDCl$_3$) δ 0.54-0.62 (2H, m), 0.76-0.86 (2H, m), 2.29 (3H, s), 2.77-2.84 (1H, m), 6.61 (1H, s), 6.70 (1H, d, J=10.24 Hz), 7.18 (1H, d, J=7.96 Hz), 7.34-7.52 (4H, m), 7.68 (1H, s), 8.00-8.06 (2H, m), 8.41 (1H, s)

EXAMPLE 19

N-{5-[(Cyclopropylamino)carbonyl]-2-methylphenyl}-1-(2-methylphenyl)-6-oxo-1,6-dihydro-3-pyridinecarboxamide was obtained according to a similar manner to Example 18.

$^1$H-NMR (CDCl$_3$) δ 0.53-0.61 (2H, m), 0.76-0.88 (2H, m), 2.17 (3H, s), 2.35 (3H, s), 2.76-2.84 (1H, m), 6.49 (1H, s), 6.69 (1H, d, J=9.56), 7.18-7.46 (6H, m), 7.74 (1H, s), 7.97 (1H, dd, J=9.76 and 2.72 Hz), 8.18 (1H, d, J=2.44 Hz), 8.25 (1H, s)

EXAMPLE 20

To a solution of 1-tert-butyl-6-oxo-1,6-dihydro-3-pyridinecarboxylic acid (30 mg) in DMF (0.6 mL) were added 3-amino-N-cyclopropyl-4-methylbenzamide (44 mg), HATU (88 mg) and iPr$_2$NEt (89 mg), and the mixture was stirred under a nitrogen atmosphere at room temperature for 3 hr. The reaction mixture was diluted with EtOAc (3 mL) and the resulting mixture was washed with 1 M HCl (3 mL×2), water (3 mL), saturated aqueous NaHCO$_3$ (3 mL) and brine successively, dried over MgSO$_4$, filtered and evaporated in vacuo. The residue was purified by preparative thin layer chromatography eluting with 10% MeOH in CH$_2$Cl$_2$ to give N-{5-[(cyclopropylamino)carbonyl]-2-methylphenyl}-1-tert-butyl-6-oxo-1,6-dihydro-3-pyridinecarboxamide (27 mg).

Mass ESI (+) 390 (M+Na)

¹H-NMR (CD₃OD) δ 0.58-0.66 (2H, m), 0.75-0.85 (2H, m), 1.74 (9H, s), 2.79-2.87 (1H, m), 4.60 (2H, s), 6.51 (1H, d, J=9.34 Hz), 7.37 (1H, d, J=7.98 Hz), 7.63 (1H, dd, J=7.94 and 1.86 Hz), 7.74 (1H, d, J=1.72 Hz), 7.98 (1H, dd, J=9.42 and 2.48 Hz), 8.55 (1H, d, J=2.42 Hz)

EXAMPLE 21

N-{5-[(Cyclopropylamino)carbonyl]-2-methylphenyl}-1-(2,6-dimethylphenyl)-6-oxo-1,6-dihydro-3-pyridinecarboxamide was obtained according to a similar manner to Example 20.
Mass ESI (+) 438 (M+Na)
¹H-NMR (CD₃OD) δ 0.57-0.64 (2H, m), 0.74-0.84 (2H, m), 2.11 (6H, s), 2.77-2.85 (1H, m), 6.78 (1H, d, J=10.44 Hz), 7.23-7.37 (4H, m), 7.62 (1H, dd, J=7.96 and 1.88 Hz), 7.73 (1H, d, J=1.84 Hz), 8.19-8.25 (2H, m)

EXAMPLE 22

N-{5-[(Cyclopropylamino)carbonyl]-2-methylphenyl}-1-(2,6-difluorophenyl)-6-oxo-1,6-dihydro-3-pyridinecarboxamide was obtained according to a similar manner to Example 20.
Mass ESI (+) 446 (M+Na)
¹H-NMR (CD₃OD) δ 0.57-0.67 (2H, m), 0.70-0.84 (2H, m), 2.77-2.88 (1H, m), 6.75 (1H, d, J=9.72 Hz), 7.22-7.37 (3H, m), 7.55-7.70 (2H, m), 7.74 (1H, d, J=1.60 Hz), 8.18 (1H, dd, J=9.72 and 2.56 Hz), 8.39 (1H, d, J=2.22 Hz)

EXAMPLE 23

N-{5-[(Cyclopropylamino)carbonyl]-2-methylphenyl}-1-(2-chloro-6-fluorophenyl)-6-oxo-1,6-dihydro-3-pyridinecarboxamide was obtained according to a similar manner to Example 20.
Mass ESI (+) 462 (M+Na)
¹H-NMR (CD₃OD) δ 0.57-0.65 (2H, m), 0.70-0.84 (2H, m), 2.77-2.98 (1H, m), 6.75 (1H, d, J=9.62 Hz), 7.34-7.43 (2H, m), 7.54-7.65 (3H, m), 7.74 (1H, d, J=1.74 Hz), 8.20 (1H, dd, J=9.64 and 2.58 Hz), 8.33 (1H, d, J=2.46 Hz)

EXAMPLE 24

N-{5-[(Cyclopropylamino)carbonyl]-2-methylphenyl}-1-(1-phenylethyl)-6-oxo-1,6-dihydro-3-pyridinecarboxamide was obtained according to a similar manner to Example 20.
Mass ESI (+) 438 (M+Na)
¹H-NMR (CD₃OD) δ 0.56-0.66 (2H, m), 0.69-0.83 (2H, m), 1.82 (3H, d, J=7.16 Hz), 2.25 (3H, s), 2.76-2.87 (1H, m), 6.33 (1H, q, J=7.11 Hz), 6.64 (1H, d, =9.50 Hz), 7.32-7.39 (5H, m), 7.62 (1H, dd, J=8.02 and 1.40 Hz), 7.68 (1H, s), 8.03 (1H, dd, J=9.47 and 2.43 Hz), 8.27 (1H, d, J=2.35 Hz)

EXAMPLE 25

To a solution of 1-(2,6-dichlorophenyl)-6-oxo-1,6-dihydro-3-pyridinecarboxylic acid (30 mg) in DMF (0.6 mL) were added N-(3-amino-4-methylphenyl)cyclopropanecarboxamide (30 mg), HATU (60 mg) and iPr₂NEt (62 mg) successively, and the mixture was stirred under a nitrogen atmosphere at room temperature for 16 hr. The reaction mixture was diluted with EtOAc (3 mL), and the resulting mixture was washed with 1 M HCl (3 mL×2), saturated aqueous NaHCO₃ (3 mL×2) and brine successively, dried over MgSO₄ and evaporated in vacuo. The residue was triturated with 10% MeOH in CH₂Cl₂, and the precipitates produced were collected by filtration to give N-{5-[(cyclopropylcarbonyl)amino]-2-methylphenyl}-1-(2,6-dichlorophenyl)-6-oxo-1,6-dihydro-3-pyridinecarboxamide (25 mg).
Mass ESI (+) 478 (M+Na)
¹H-NMR (DMSO-d₆) δ 0.76 (4H, d, J=6.08 Hz), 1.70-1.80 (1H, m), 2.13 (3H, s), 6.68 (1H, d, J=9.70 Hz), 7.15 (1H, d, J=8.34 Hz), 7.33 (1H, dd, J=8.20 and 2.02 Hz), 7.57-7.65 (2H, m), 7.74 (1H, s), 7.78 (1H, d, J=1.48 Hz), 8.13 (1H, dd, J=9.66 and 2.54 Hz), 8.40 (1H, d, J=2.42 Hz), 9.69 (1H, s), 10.16 (1H, s)

EXAMPLE 26

To a solution of 1-(2,6-dichlorophenyl)-6-oxo-1,6-dihydro-3-pyridinecarboxylic acid (35 mg) and 1-(3-amino-4-methylphenyl)-3-[3-tert-butyl-1-(4-methylphenyl)-1H-pyrazol-5-yl]urea (70 mg) in DMF (1 mL) were added HATU (71 mg) and iPr₂NEt (96 mg) successively under a nitrogen atmosphere, and the mixture was stirred at room temperature for 16 hr. The reaction mixture was diluted with EtOAc (5 mL) and the resulted mixture was successively washed with 1M HCl (5 mL×2), saturated aqueous NaHCO₃ (5 mL×2) and brine, dried over MgSO₄, filtered and evaporated in vacuo. The residue was purified by silica gel column chromatography eluting with 5% MeOH in CH₂Cl₂. The isolated material was triturated with CH₂Cl₂, and the precipitates were collected by filtration to give N-[5-[({[3-tert-butyl-1-(4-methylphenyl)-1H-pyrazol-5-yl]amino}carbonyl)amino]-2-methylphenyl}-1-(2,6-dichlorophenyl)-6-oxo-1,6-dihydro-3-pyridinecarboxamide (34 mg).
Mass ESI (+) 665 (M+Na)
¹H-NMR (DMSO-d₆) δ 1.26 (9H, s), 2.12 (3H, s), 2.36 (3H, s), 6.34 (1H, s), 6.69 (1H, d, J=9.72 Hz), 7.06-7.15 (2H, m), 7.32 (2H, d, J=8.52 Hz), 7.39 (2H, d, J=8.62 Hz), 7.53 (1H, d, J=1.52 Hz), 7.61 (1H, dd, J=9.16 and 6.90 Hz), 7.74 (1H, s), 7.78 (1H, d, J=1.56 Hz), 8.13 (1H, dd, J=9.68 and 2.60 Hz), 8.31 (1H, br s), 8.40 (1H, d, J=2.34 Hz), 9.00 (1H, br s), 9.65 (1H, s)

EXAMPLE 27

N-{5-[(Anilinocarbonyl)amino]-2-methylphenyl}-1-(2,6-dichlorophenyl)-6-oxo-1,6-dihydro-3-pyridinecarboxamide was obtained according to a similar manner to Example 26.
Mass ESI (+) 531 (M+Na)
¹H-NMR (DMSO-d₆) δ 2.13 (3H, s), 6.70 (1H, d, J=9.64 Hz), 6.95 (1H, t, J=7.40 Hz), 7.15-7.30 (4H, m), 7.41-7.65 (4H, m), 7.74-7.78 (2H, d, J=7.54 Hz), 8.14 (1H, dd, J=9.94 and 2.44 Hz), 8.41 (1H, d, J=2.10 Hz), 8.63 (2H, d, J=4.32 Hz), 9.70 (1H, s)

EXAMPLE 28

N-(5-{[(Cyclopropylamino)carbonyl]amino}-2-methylphenyl)-1-(2,6-dichlorophenyl)-6-oxo-1,6-dihydro-3-pyridinecarboxamide was obtained according to a similar manner to Example 26.
Mass ESI (+) 493 (M+Na)
¹H-NMR (DMSO-d₆) δ 0.34-0.42 (2H, m), 0.57-0.66 (2H, m), 2.10 (3H, s), 6.34 (1H, d, J=2.32 Hz), 6.68 (1H, d, J=9.70 Hz), 7.00-7.17 (2H, m), 7.43 (1H, d, J=1.72 Hz), 7.61 (1H, dd, J=9.14 and 6.94 Hz), 7.74 (1H, s), 7.78 (1H, d, J=1.48 Hz), 8.13 (1H, dd, J=9.72 and 2.54 Hz), 8.24 (1H, s), 8.39 (1H, d, J=2.32 Hz), 9.65 (1H, s)

The following compounds could be obtained in a similar manner to Preparations, Examples and methods obvious to those skilled in the art or modified methods thereof.

EXAMPLE 29

N-{2-Bromo-5-[(cyclopropylamino)carbonyl]phenyl}-1-(2,6-dichlorophenyl)-6-oxo-1,6-dihydro-3-pyridinecarboxamide

EXAMPLE 30

N-{2-Bromo-5-[(cyclopropylamino)carbonyl]phenyl}-1-(2-chloro-6-fluorophenyl)-6-oxo-1,6-dihydro-3-pyridinecarboxamide

EXAMPLE 31

N-{2-Bromo-5-[(cyclopropylamino)carbonyl]phenyl}-1-(2,6-dimethylphenyl)-6-oxo-1,6-dihydro-3-pyridinecarboxamide

EXAMPLE 32

N-{2-Bromo-5-[(cyclopropylamino)carbonyl]phenyl}-1-(2-methylphenyl)-6-oxo-1,6-dihydro-3-pyridinecarboxamide

EXAMPLE 33

N-{2-Bromo-5-[(cyclopropylamino)carbonyl]phenyl}-1-(2,6-dimethyl-4-fluorophenyl)-6-oxo-1,6-dihydro-3-pyridinecarboxamide

EXAMPLE 34

N-[5-(Anilinocarbonyl)-2-bromophenyl]-1-(2,6-dichlorophenyl)-6-oxo-1,6-dihydro-3-pyridinecarboxamide

EXAMPLE 35

N-[5-(Anilinocarbonyl)-2-bromophenyl]-1-(2,6-difluorophenyl)-6-oxo-1,6-dihydro-3-pyridinecarboxamide

EXAMPLE 36

N-[5-(Anilinocarbonyl)-2-bromophenyl]-1-(2,6-dimethylphenyl)-6-oxo-1,6-dihydro-3-pyridinecarboxamide

EXAMPLE 37

N-[5-(Anilinocarbonyl)-2-chlorophenyl]-1-(2,6-dichlorophenyl)-6-oxo-1,6-dihydro-3-pyridinecarboxamide

EXAMPLE 38

N-[5-(Anilinocarbonyl)-2-chlorophenyl]-1-(2,6-difluorophenyl)-6-oxo-1,6-dihydro-3-pyridinecarboxamide

EXAMPLE 39

N-[5-(Anilinocarbonyl)-2-chlorophenyl]-1-(2,6-dimethylphenyl)-6-oxo-1,6-dihydro-3-pyridinecarboxamide

EXAMPLE 40

N-[5-(Anilinocarbonyl)-2-methylphenyl]-1-(2,6-dimethylphenyl)-6-oxo-1,6-dihydro-3-pyridinecarboxamide

EXAMPLE 41

N-{2-Bromo-5-[(cyclopropylcarbonyl)amino]phenyl}-1-(2,6-dichlorophenyl)-6-oxo-1,6-dihydro-3-pyridinecarboxamide

EXAMPLE 42

N-{2-Bromo-5-[(cyclopropylcarbonyl)amino]phenyl}-1-(2,6-difluorophenyl)-6-oxo-1,6-dihydro-3-pyridinecarboxamide

EXAMPLE 43

N-{2-Bromo-5-[(cyclopropylcarbonyl)amino]phenyl}-1-(2,6-dimethylphenyl)-6-oxo-1,6-dihydro-3-pyridinecarboxamide

EXAMPLE 44

N-{2-Chloro-5-[(cyclopropylcarbonyl)amino]phenyl}-1-(2,6-dichlorophenyl)-6-oxo-1,6-dihydro-3-pyridinecarboxamide

EXAMPLE 45

N-{2-Chloro-5-[(cyclopropylcarbonyl)amino]phenyl}-1-(2,6-difluorophenyl)-6-oxo-1,6-dihydro-3-pyridinecarboxamide

EXAMPLE 46

N-{2-Chloro-5-[(cyclopropylcarbonyl)amino]phenyl}-1-(2,6-dimethylphenyl)-6-oxo-1,6-dihydro-3-pyridinecarboxamide

EXAMPLE 47

N-{2-Bromo-5-[(1H-pyrazol-3-ylamino)carbonyl]phenyl}-1-(2,6-difluorophenyl)-6-oxo-1,6-dihydro-3-pyridinecarboxamide

EXAMPLE 48

N-{2-Bromo-5-[(1-methyl-1H-pyrazol-5-ylamino)carbonyl]phenyl}-1-(2,6-difluorophenyl)-6-oxo-1,6-dihydro-3-pyridinecarboxamide

EXAMPLE 49

N-{2-Bromo-5-[(1-methyl-1H-pyrazol-3-ylamino)carbonyl]phenyl}-1-(2,6-difluorophenyl)-6-oxo-1,6-dihydro-3-pyridinecarboxamide

EXAMPLE 50

N-{2-Bromo-5-[(5-methyl-1,3,4-oxadiazol-2-ylamino)carbonyl]phenyl}-1-(2,6-difluorophenyl)-6-oxo-1,6-dihydro-3-pyridinecarboxamide

EXAMPLE 51

N-{2-Bromo-5-[(methoxyamino)carbonyl]phenyl}-1-(2,6-difluorophenyl)-6-oxo-1,6-dihydro-3-pyridinecarboxamide

EXAMPLE 52

N-{2-Bromo-5-[(isoxazol-3-ylamino)carbonyl]phenyl}-1-(2,6-difluorophenyl)-6-oxo-1,6-dihydro-3-pyridinecarboxamide

EXAMPLE 53

N-{2-Bromo-5-[(pyridin-3-ylamino)carbonyl]phenyl}-1-(2,6-difluorophenyl)-6-oxo-1,6-dihydro-3-pyridinecarboxamide

EXAMPLE 54

1-(2,6-Difluorophenyl)-N-{2-methyl-5-[(1H-pyrazol-3-ylamino)carbonyl]phenyl}-6-oxo-1,6-dihydro-3-pyridinecarboxamide

EXAMPLE 55

1-(2,6-Difluorophenyl)-N-{2-methyl-5-[(1-methyl-1H-pyrazol-5-ylamino)carbonyl]phenyl}-6-oxo-1,6-dihydro-3-pyridinecarboxamide

EXAMPLE 56

1-(2,6-Difluorophenyl)-N-{2-methyl-5-[(1-methyl-1H-pyrazol-3-ylamino)carbonyl]phenyl}-6-oxo-1,6-dihydro-3-pyridinecarboxamide

EXAMPLE 57

1-(2,6-Difluorophenyl)-N-{2-methyl-5-[(5-methyl-1,3,4-oxadiazol-2-ylamino)carbonyl]phenyl}-6-oxo-1,6-dihydro-3-pyridinecarboxamide

EXAMPLE 58

1-(2,6-Difluorophenyl)-N-{5-[(methoxyamino)carbonyl]-2-methylphenyl}-6-oxo-1,6-dihydro-3-pyridinecarboxamide

EXAMPLE 59

1-(2,6-Difluorophenyl)-N-{5-[(isoxazol-3-ylamino)carbonyl]-2-methylphenyl}-6-oxo-1,6-dihydro-3-pyridinecarboxamide

EXAMPLE 60

1-(2,6-Difluorophenyl)-N-{2-methyl-5-[(pyridin-3-ylamino)carbonyl]phenyl}-6-oxo-1,6-dihydro-3-pyridinecarboxamide The compounds of the present invention are listed in the following tables.

No.: Example No.

| No. | Structure |
|---|---|
| 5 | 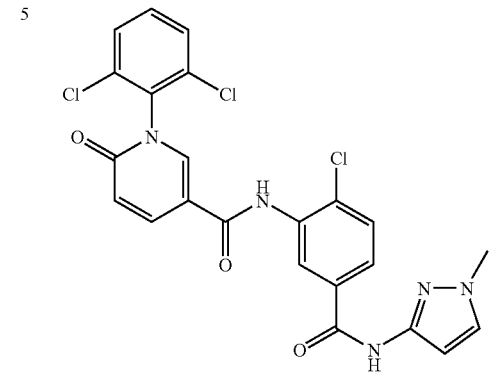 |
| 6 | 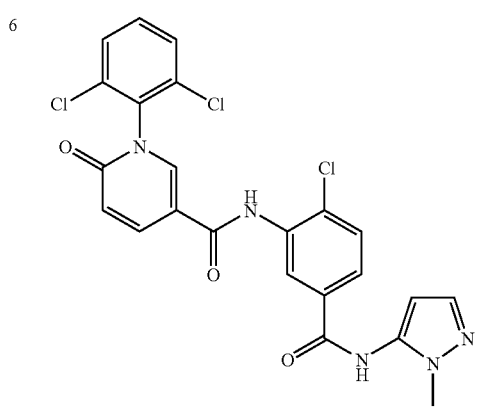 |
| 7 | 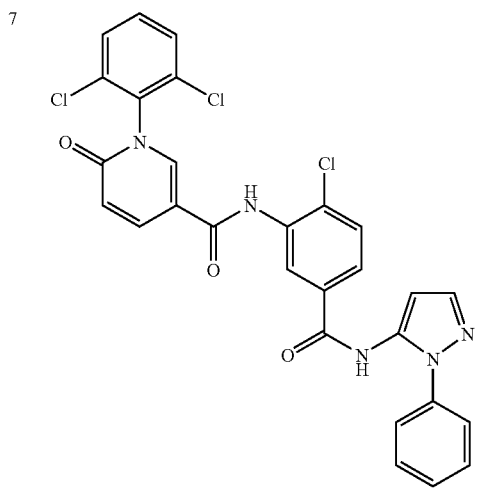 |
| No. | Structure |
|---|---|
| 8 | 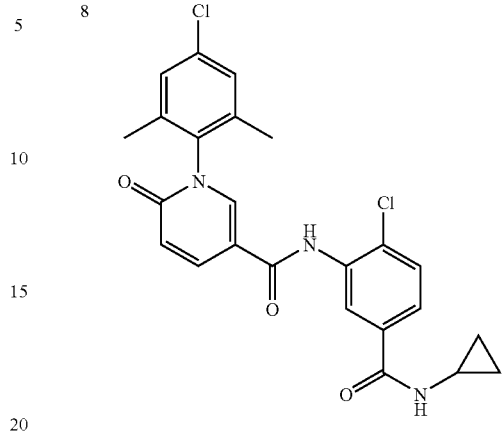 |
| 9 | 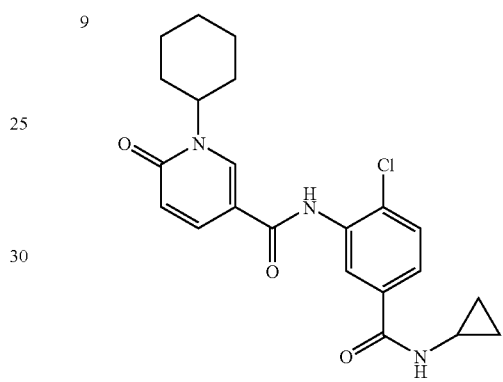 |
| 10 | 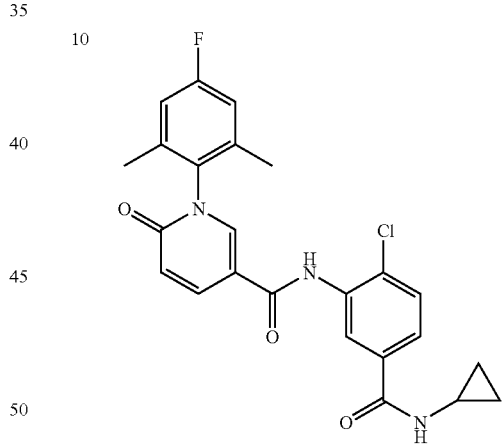 |
| 11 | 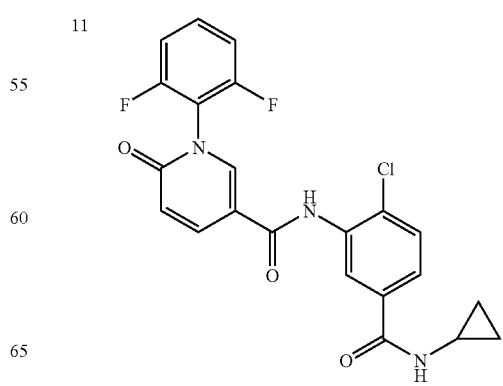 |

-continued

| No. | Structure |
|---|---|
| 12 | 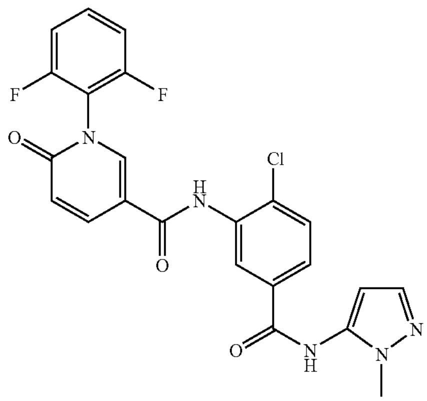 |
| 13 | 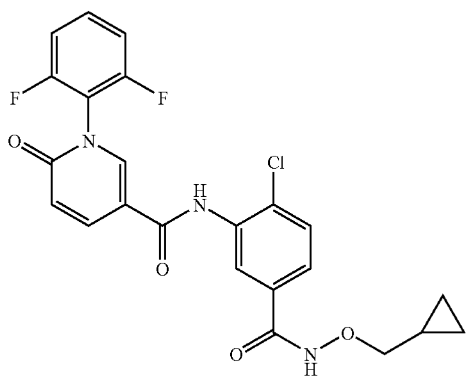 |
| 14 | 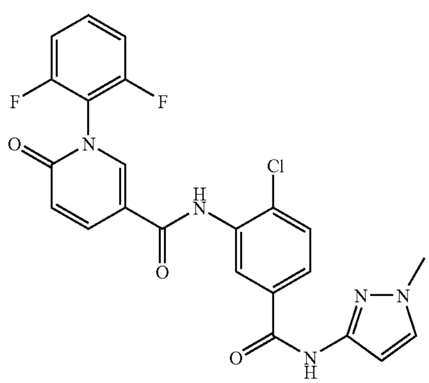 |
| 15 | 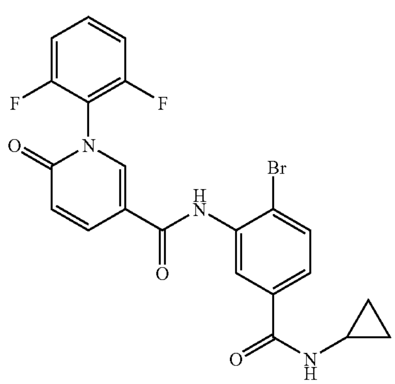 |

-continued

| No. | Structure |
|---|---|
| 16 | 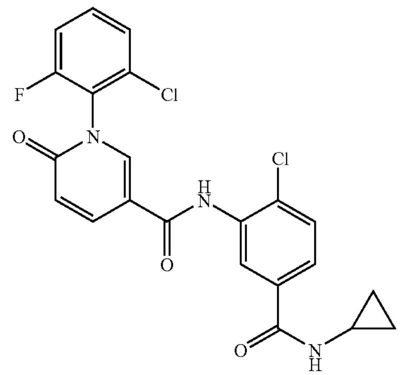 |
| 17 | 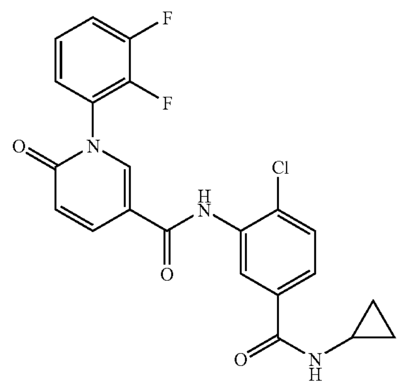 |
| 18 | 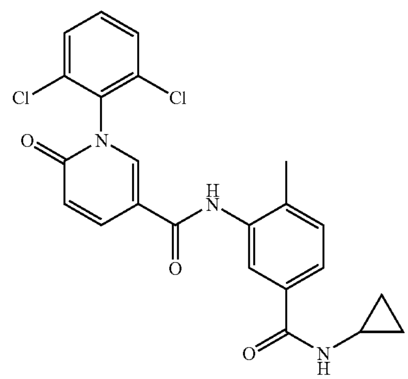 |
| 19 | 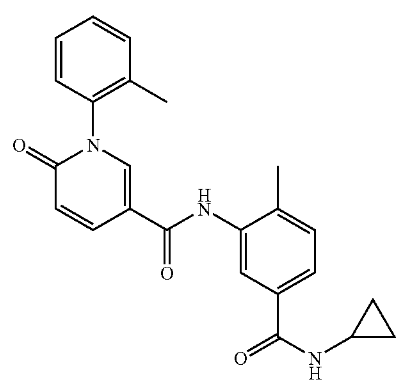 |

| No. | Structure |
|---|---|
| 20 | 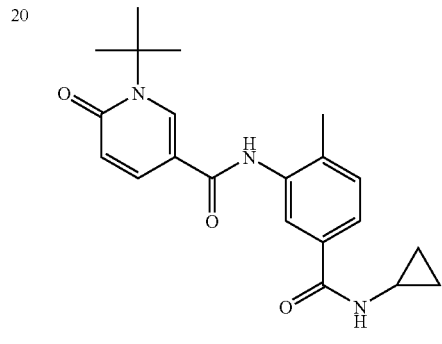 |
| 21 | 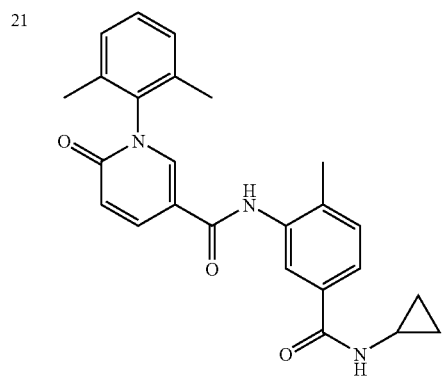 |
| 22 | 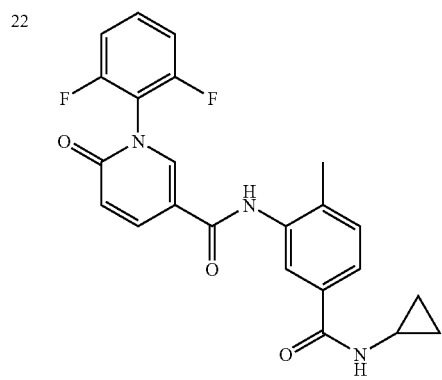 |
| 23 | 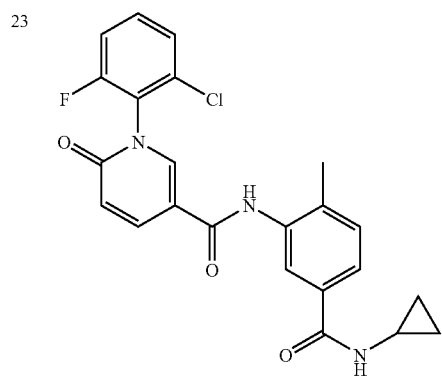 |
| No. | Structure |
|---|---|
| 24 | 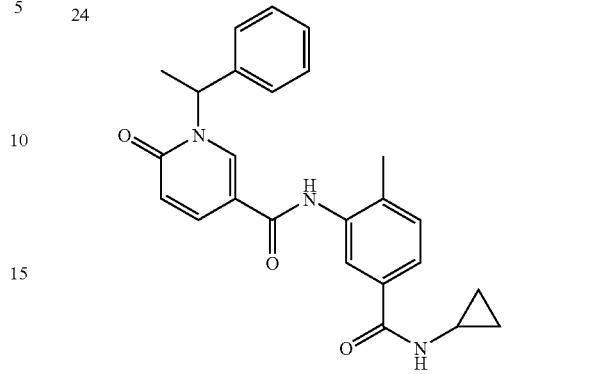 |
| 25 | 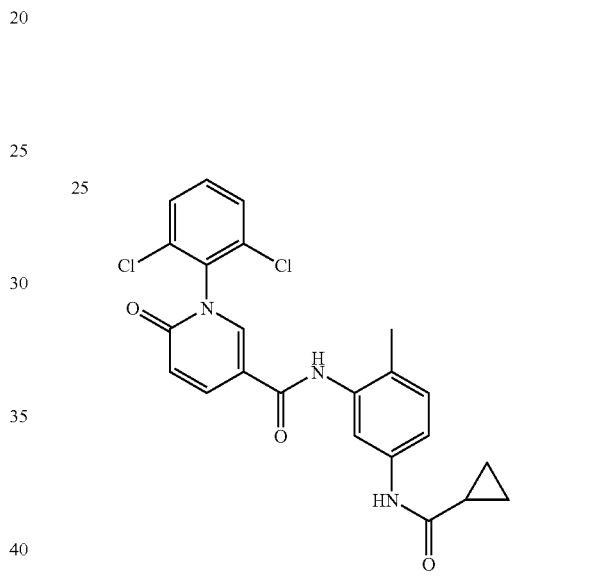 |
| 26 | 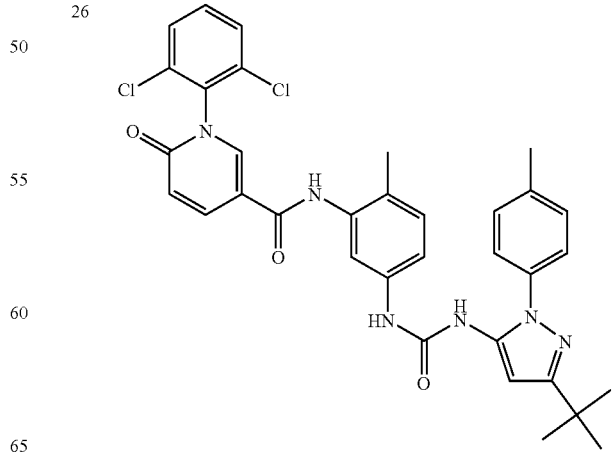 |

| No. | Structure |
|---|---|
| 27 | (2,6-dichlorophenyl pyridinone carboxamide with 4-methyl-3-(3-phenylureido)phenyl) |
| 28 | (2,6-dichlorophenyl pyridinone carboxamide with 4-methyl-3-(3-cyclopropylureido)phenyl) |
| 29 | (2,6-dichlorophenyl pyridinone carboxamide with 2-bromo-5-(cyclopropylcarbamoyl)phenyl) |
| 30 | (2-chloro-6-fluorophenyl pyridinone carboxamide with 2-bromo-5-(cyclopropylcarbamoyl)phenyl) |
| 31 | (2,6-dimethylphenyl pyridinone carboxamide with 2-bromo-5-(cyclopropylcarbamoyl)phenyl) |
| 32 | (2-methylphenyl pyridinone carboxamide with 2-bromo-5-(cyclopropylcarbamoyl)phenyl) |
| 33 | (4-fluoro-2,6-dimethylphenyl pyridinone carboxamide with 2-bromo-5-(cyclopropylcarbamoyl)phenyl) |
| 34 | (2,6-dichloropyridin-3-yl pyridinone carboxamide with 2-bromo-5-(phenylcarbamoyl)phenyl) |

| No. | Structure |
|---|---|
| 35 | 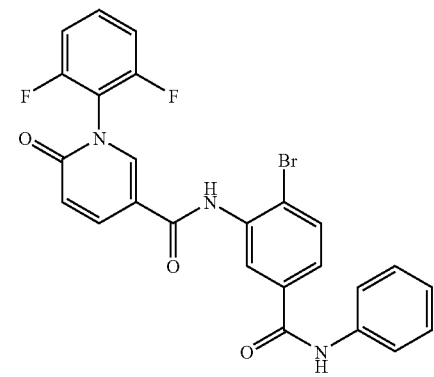 |
| 36 | 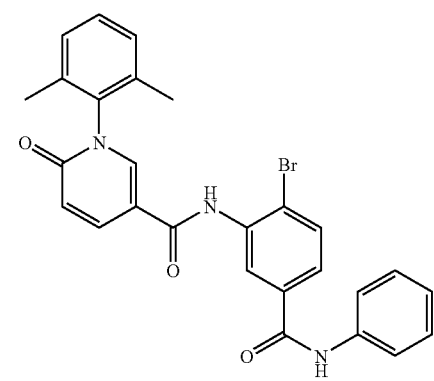 |
| 37 | 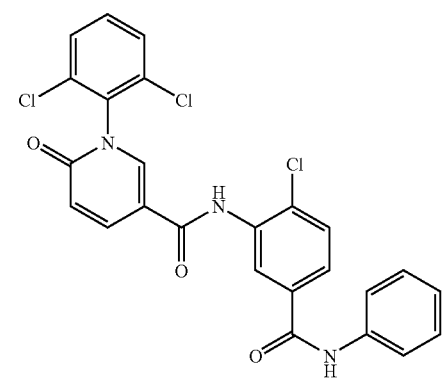 |
| 38 | 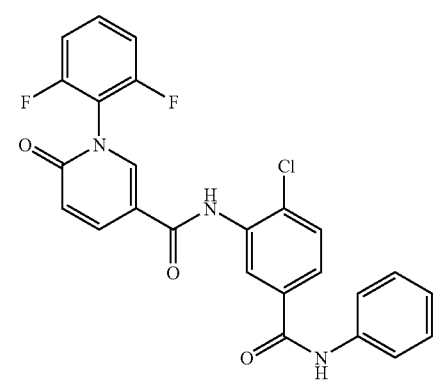 |
| 39 | 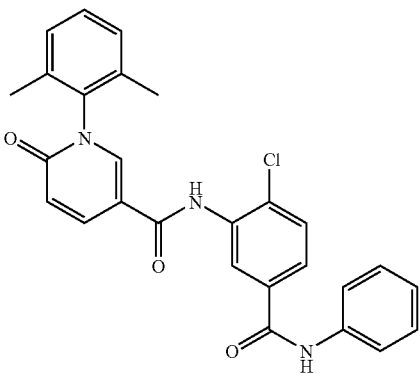 |
| 40 | 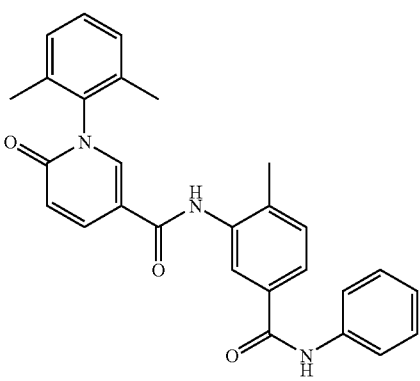 |
| 41 | 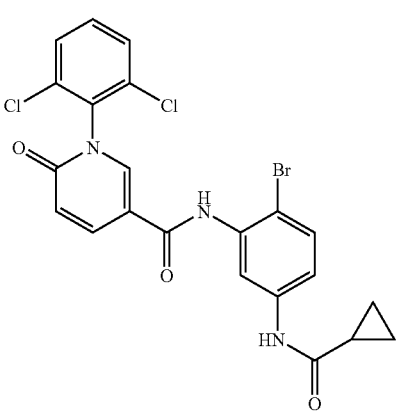 |
| 42 | 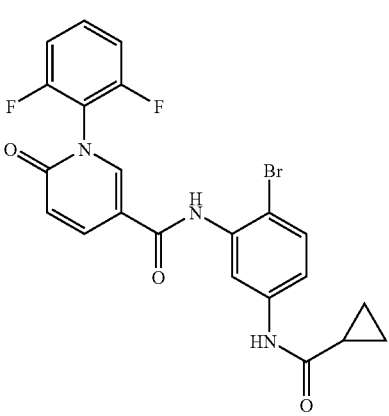 |

-continued

| No. | Structure |
|-----|-----------|
| 43 | 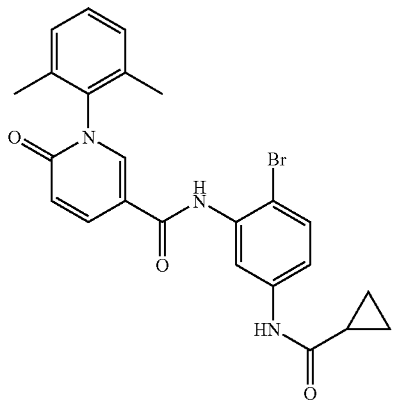 |
| 44 | 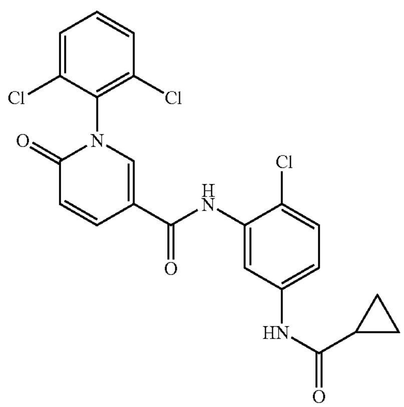 |
| 45 | 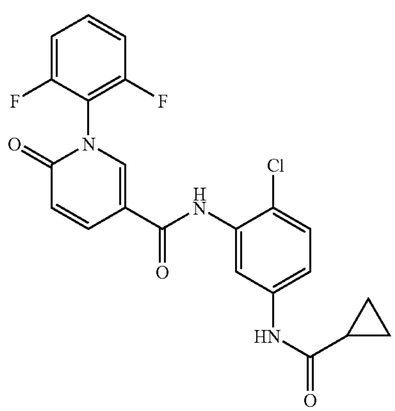 |
| 46 | 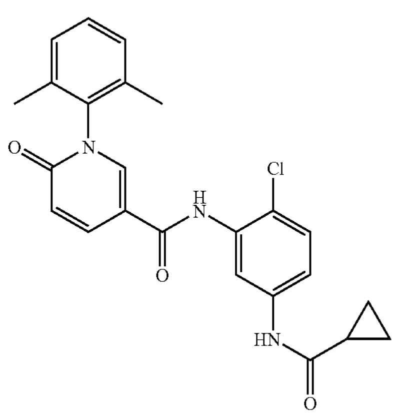 |

-continued

| No. | Structure |
|-----|-----------|
| 47 | 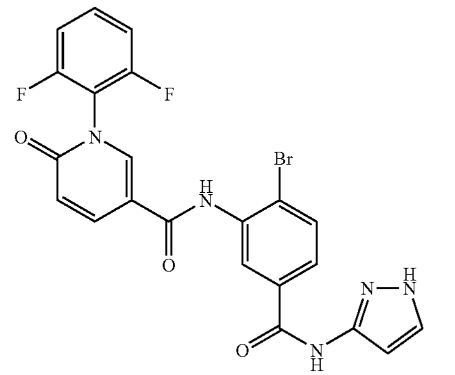 |
| 48 | 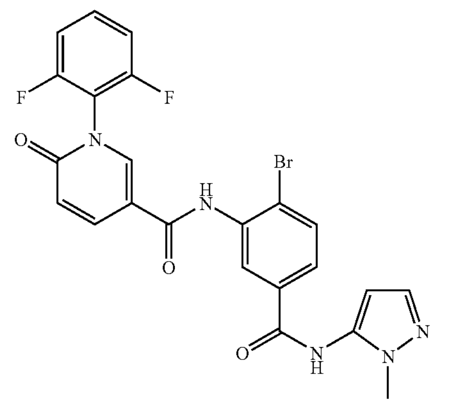 |
| 49 | 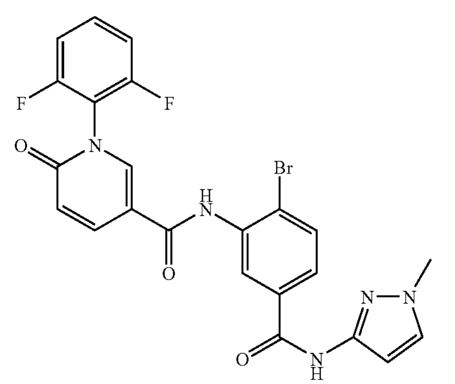 |
| 50 | 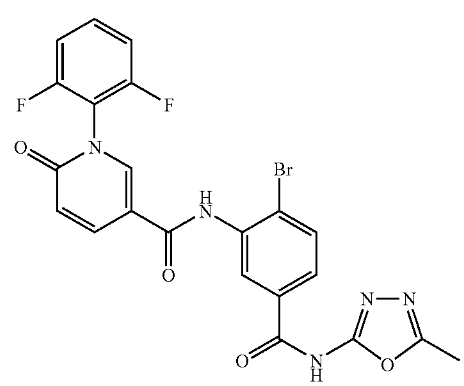 |

-continued
| No. | Structure |
|---|---|
| 51 | 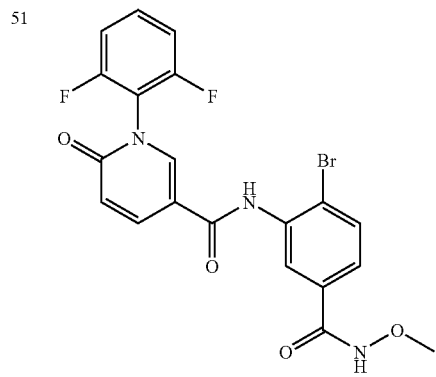 |
| 52 | 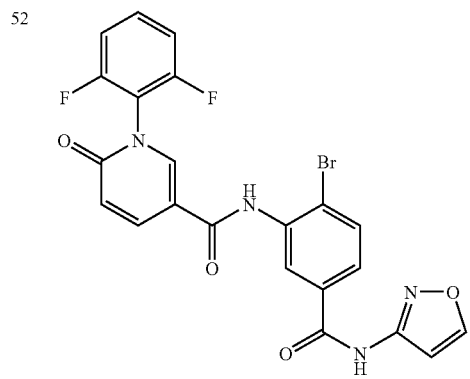 |
| 53 | 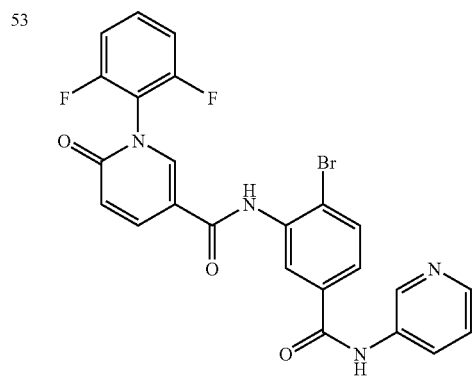 |
| 54 | 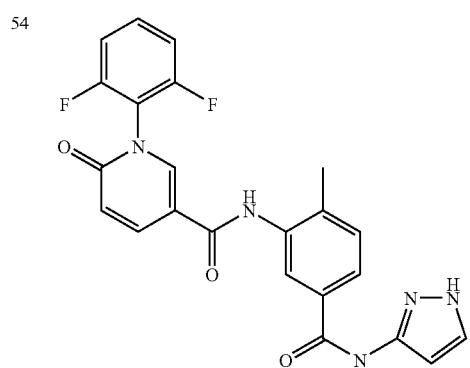 |
| 55 | 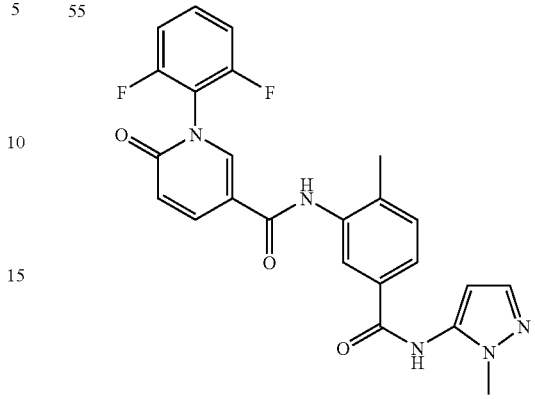 |
| 56 | 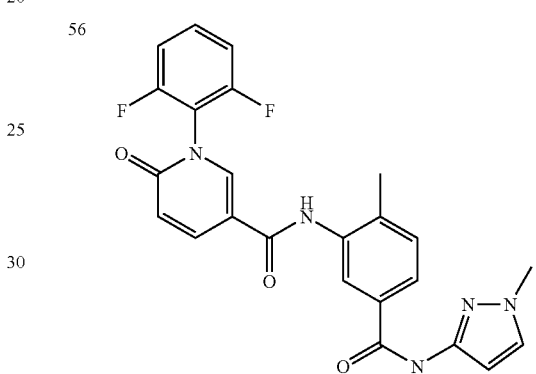 |
| 57 | 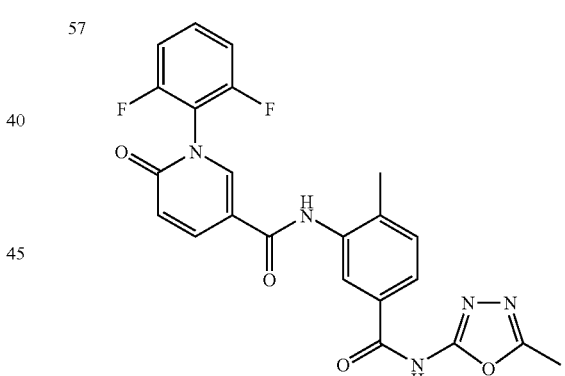 |
| 58 | 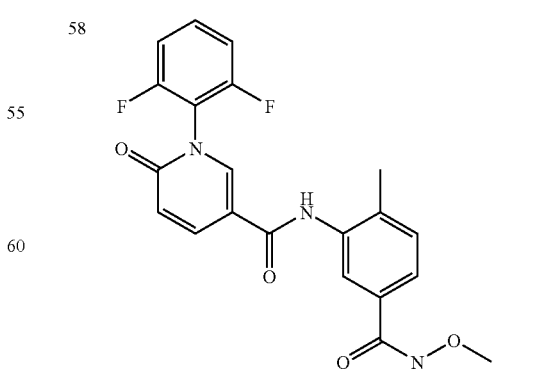 |

| No. | Structure |
|---|---|
| 59 | 2,6-difluorophenyl-N-oxo-pyridine carboxamide linked to methylphenyl carboxamide-isoxazole |
| 60 | 2,6-difluorophenyl-N-oxo-pyridine carboxamide linked to methylphenyl carboxamide-pyridine |

The invention claimed is:

1. A compound represented by the formula (I):

(I) [structure of 1-R¹-6-oxo-pyridine-3-carboxamide-N-(3-R²,5-R³-phenyl)]

wherein

R¹ is lower alkyl, cycloalkyl or aromatic hydrocarbon ring, each of which is optionally substituted with one or more substituents;

R² is halogen atom, lower alkyl, halo(lower)alkyl or lower alkoxy; and

R³ is (1) a group represented by the formula:

[CH₃-C(=O)-NH-R⁴]

wherein

R⁴ is lower alkyl, lower alkoxy, cycloalkyl, aromatic hetero ring, non-aromatic hetero ring or aromatic hydrocarbon ring, each of which is optionally substituted with one or more substituents;

(2) a group represented by the formula:

[CH₃-NH-C(=O)-NH-R⁵]

wherein

R⁵ is lower alkyl, cycloalkyl, aromatic hydrocarbon ring, aromatic hetero ring or non-aromatic hetero ring, each of which is optionally substituted with one or more substituents;

(3) a group represented by the formula:

[CH₃-NH-C(=O)-R⁶]

wherein

R⁶ is lower alkyl, cycloalkyl, aromatic hydrocarbon ring or non-aromatic hetero ring, each of which is optionally substituted with one or more substituents; or (4) a group selected from halogen atom, carboxy, hydroxy and lower alkoxy, or a salt thereof.

2. The compound of claim 1, wherein

R¹ is lower alkyl, cycloalkyl or aromatic hydrocarbon ring, each of which is optionally substituted with one or more substituents;

R² is halogen atom or lower alkyl; and

R³ is (1) a group represented by the formula:

[CH₃-C(=O)-NH-R⁴]

wherein

R⁴ is lower alkoxy, cycloalkyl, aromatic hetero ring or aromatic hydrocarbon ring, each of which is optionally substituted with one or more substituents, (2) a group represented by the formula:

[CH₃-NH-C(=O)-NH-R⁵]

wherein

R⁵ is cycloalkyl, aromatic hydrocarbon ring or aromatic hetero ring, each of which is optionally substituted with one or more substituents; or (3) a group represented by the formula:

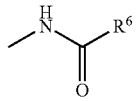

wherein
$R^6$ is cycloalkyl, which is optionally substituted with one or more substituents, or a salt thereof.

3. The compound of claim 2, wherein
$R^1$ is
(1) $(C_{1-6})$ alkyl optionally substituted with one $(C_{6-16})$ aryl,
(2) $(C_{3-7})$ cycloalkyl, or
(3) $(C_{6-16})$ aryl optionally substituted with 1 to 3 substituents selected from halogen atom, $(C_{1-6})$alkyl and $(C_{6-16})$ aryl;

$R^2$ is halogen atom or $(C_{1-6})$alkyl, and
$R^3$ is
(1) a group represented by the formula:

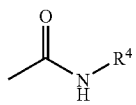

wherein
$R^4$ is $(C_{1-6})$alkoxy, $(C_{3-7})$ cycloalkyl, 5- to 14-membered aromatic hetero ring or $(C_{6-16})$aryl, each of which is optionally substituted with 1 to 3 substituents selected from $(C_1$—6) alkyl, $(C_{3-7})$ cycloalkyl and $(C_{6-16})$ aryl,
(2) a group represented by the formula:

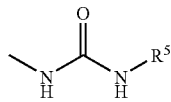

wherein
$R^5$ is $(C_{3-7})$cycloalkyl, $(C_{6-16})$aryl or 5- to 14-membered aromatic hetero ring, each of which is optionally substituted with 1 to 3 substituents selected from $(C_{1-6})$ alkyl and $(C_{6-16})$aryl which is optionally substituted with $(C_{1-6})$alkyl, or
(3) a group represented by the formula:

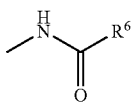

wherein
$R^6$ is $(C_{3-7})$cycloalkyl, or a salt thereof.

4. A pharmaceutical composition comprising the compound of claim 1 or a pharmaceutically acceptable salt thereof in admixture with a pharmaceutically acceptable carrier.

5. The pharmaceutical composition of claim 4, which is for the prevention or the treatment of a disease selected from the group consisting of pain, rheumatoid arthritis, other conditions associated with inflammation, Crohn's disease, inflammatory bowel disease and psoriasis.

6. A method for preventing or treating a disease selected from the group consisting of pain, rheumatoid arthritis, other conditions associated with inflammation, Crohn's disease, inflammatory bowel disease and psoriasis, which comprises administering an effective amount of the compound of claim 1 or a pharmaceutically acceptable salt thereof to a mammal in need thereof.

* * * * *

UNITED STATES PATENT AND TRADEMARK OFFICE
CERTIFICATE OF CORRECTION

PATENT NO. : 8,173,684 B2
APPLICATION NO. : 12/597926
DATED : May 8, 2012
INVENTOR(S) : Chiyoshi Kasahara et al.

It is certified that error appears in the above-identified patent and that said Letters Patent is hereby corrected as shown below:

Column 12, line 29: "difluorolphenyl" should read --difluorophenyl--

Column 17, line 21: "(4H), m)" should read --(4H, m)--

Signed and Sealed this
Seventh Day of August, 2012

David J. Kappos
*Director of the United States Patent and Trademark Office*